United States Patent
Kar et al.

(10) Patent No.: US 10,278,583 B2
(45) Date of Patent: May 7, 2019

(54) SYSTEMS AND METHODS FOR MEASURING CARDIAC STRAIN

(71) Applicant: WASHINGTON UNIVERSITY, St. Louis, MO (US)

(72) Inventors: Julia Kar, St. Louis, MO (US); Michael K. Pasque, St. Louis, MO (US); Brian P. Cupps, St. Louis, MO (US)

(73) Assignee: Washington University, St. Louis, MO (US)

( * ) Notice: Subject to any disclaimer, the term of this patent is extended or adjusted under 35 U.S.C. 154(b) by 87 days.

(21) Appl. No.: 15/520,991

(22) PCT Filed: Oct. 22, 2015

(86) PCT No.: PCT/US2015/056938
§ 371 (c)(1),
(2) Date: Apr. 21, 2017

(87) PCT Pub. No.: WO2016/065159
PCT Pub. Date: Apr. 28, 2016

(65) Prior Publication Data
US 2018/0116521 A1 May 3, 2018

Related U.S. Application Data

(60) Provisional application No. 62/067,704, filed on Oct. 23, 2014.

(51) Int. Cl.
*G06K 9/00* (2006.01)
*A61B 5/00* (2006.01)
(Continued)

(52) U.S. Cl.
CPC ............ *A61B 5/0044* (2013.01); *A61B 5/055* (2013.01); *G01R 33/5608* (2013.01);
(Continued)

(58) Field of Classification Search
CPC ...... G16H 30/40; A61B 5/055; A61B 5/0044; A61B 2576/023; G01R 33/5608;
(Continued)

(56) References Cited

U.S. PATENT DOCUMENTS 6,757,423 B1 * 6/2004 Amini .................... G06T 7/246
382/128
7,495,438 B2 * 2/2009 Prince ................... A61B 5/055
324/309
(Continued)

OTHER PUBLICATIONS

International Search Report and Written Opinion of International Application No. PCT/US2015/056938, dated Feb. 18, 2016, 6 pages.
(Continued)

*Primary Examiner* — Shefali D Goradia
(74) *Attorney, Agent, or Firm* — Armstrong Teasdale LLP

(57) ABSTRACT

A method for rapid computation of three-dimensional displacement and Lagrange strain in a high resolution filed of phase data obtained with Displacement Encoding with Stimulated Echoes (DENSE) in magnetic resonance images of the myocardium. The method includes semi-automated segmentation of a region of a heart, phase unwrapping the images in three dimensions, and a custom radial point interpolation method (RPIM). The RPIM is a meshfree numerical analysis method that uses radial basis functions and polynomial functions to calculate the Lagrange strain of DENSE displacement data acquired from the myocardium.

21 Claims, 19 Drawing Sheets

| (51) | Int. Cl. | |
|---|---|---|
| | G06T 7/00 | (2017.01) |
| | G01R 33/563 | (2006.01) |
| | G06T 7/11 | (2017.01) |
| | G16H 30/40 | (2018.01) |
| | A61B 5/055 | (2006.01) |
| | G01R 33/56 | (2006.01) |
| | G06T 7/60 | (2017.01) |
| | G06F 19/00 | (2018.01) |
| | G01R 33/561 | (2006.01) |

(52) U.S. Cl.
CPC .  *G01R 33/56316* (2013.01); *G01R 33/56333* (2013.01); *G06T 7/0012* (2013.01); *G06T 7/11* (2017.01); *G06T 7/60* (2013.01); *G16H 30/40* (2018.01); *A61B 2576/023* (2013.01); *G01R 33/5611* (2013.01); *G06F 19/321* (2013.01); *G06T 2200/04* (2013.01); *G06T 2207/10088* (2013.01); *G06T 2207/30048* (2013.01)

(58) Field of Classification Search
CPC ........ G01R 33/56316; G01R 33/56333; G01R 33/5611; G06T 7/0012; G06T 7/60; G06T 7/11; G06T 2200/04; G06T 2207/10088; G06T 2207/30048; G06F 19/321
See application file for complete search history.

(56) References Cited

U.S. PATENT DOCUMENTS

| 7,800,366 | B1 | 9/2010 | Prince et al. | |
|---|---|---|---|---|
| 7,813,537 | B2 | 10/2010 | Epstein et al. | |
| 2007/0219442 | A1 | 9/2007 | Aletras et al. | |
| 2008/0015428 | A1* | 1/2008 | Epstein | G06T 7/215 |
| | | | | 600/410 |
| 2012/0226482 | A1 | 9/2012 | Wu et al. | |

OTHER PUBLICATIONS

Kar, J. et al., Application of Meshfree Radical Point Interpolation Method (RPIM) for Quantifying Three-Dimensional Left-Ventricular Regional Strains with Displacement ENcoding with Stimulated Echoes (DENSE) MRI and Validation in Reference to Tagged MRI, ICCM 2014, Jul. 23-30, 2014, 2 pages.

Kar, J. et al., A Validation of Two-Dimensional In Vivo Regional Strain Computed from Displacement Encoding with Stimulated Echoes (DENSE), in Referenced to Tagged Magnetic Resonance Imaging and Studies in Repeatability, Annals of Biomedical Engineering, Mar. 2014, vol. 42, No. 3, pp. 541-554.

Kar, J. et al., Three-Dimensional Regional Strain Computation Method with Displacement ENcoding with Stimulated Echoes (DENSE) in Non-Ischemic, Non-Valvular Dilated Cardiomyopathy Patients and Healthy Subjects Validated by Tagged MRI, Journal of Magnetic Resonance Imaging, 2014, pp. 1-11.

* cited by examiner

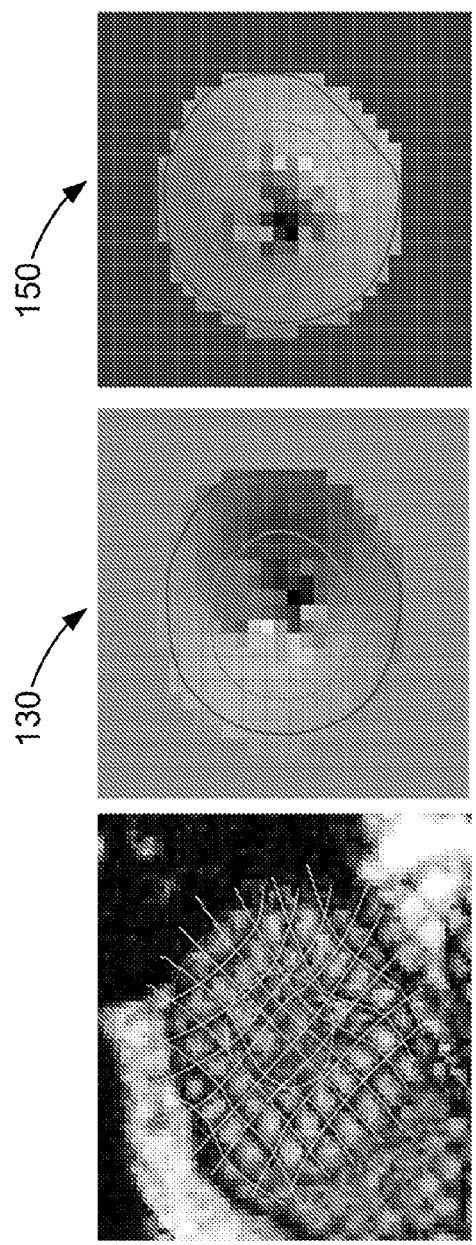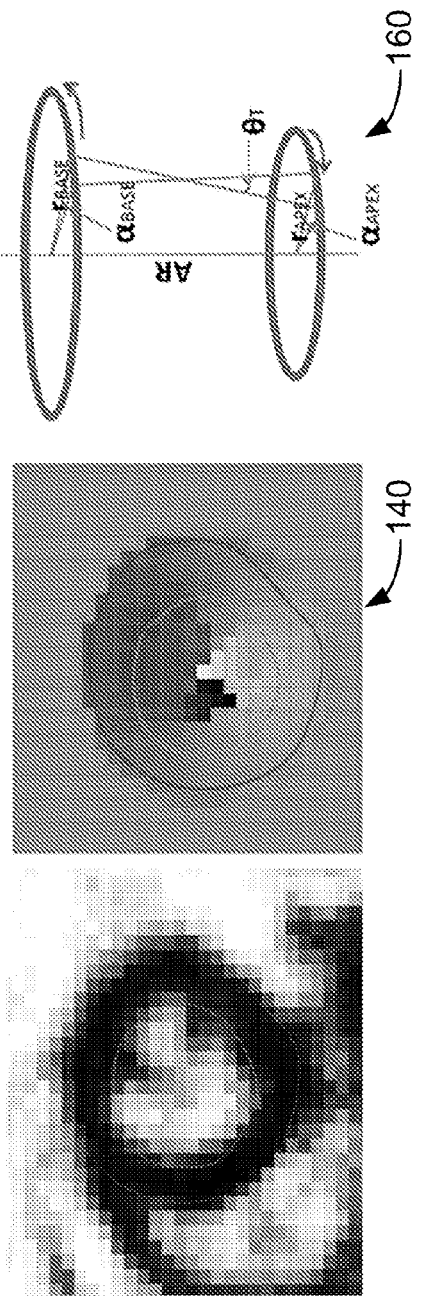
FIG. 1A
FIG. 1B
FIG. 1C
FIG. 1D
FIG. 1E
FIG. 1F

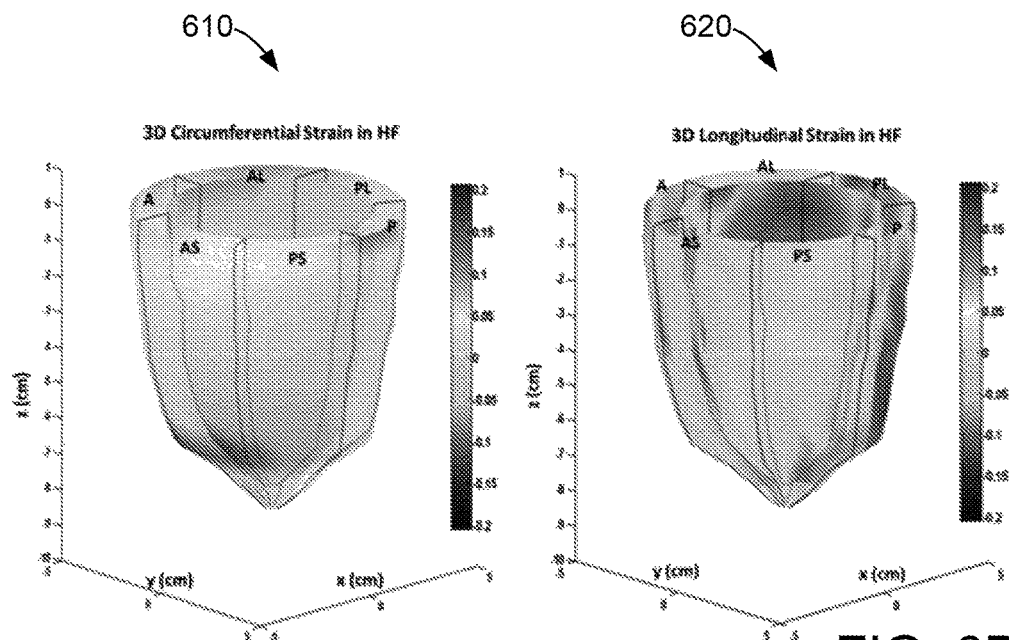
FIG. 6A
FIG. 6B
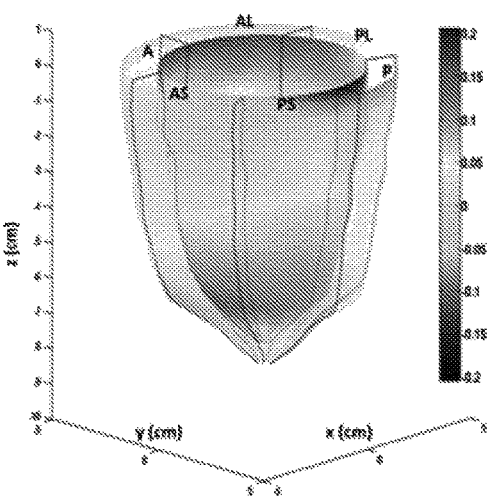
FIG. 6C

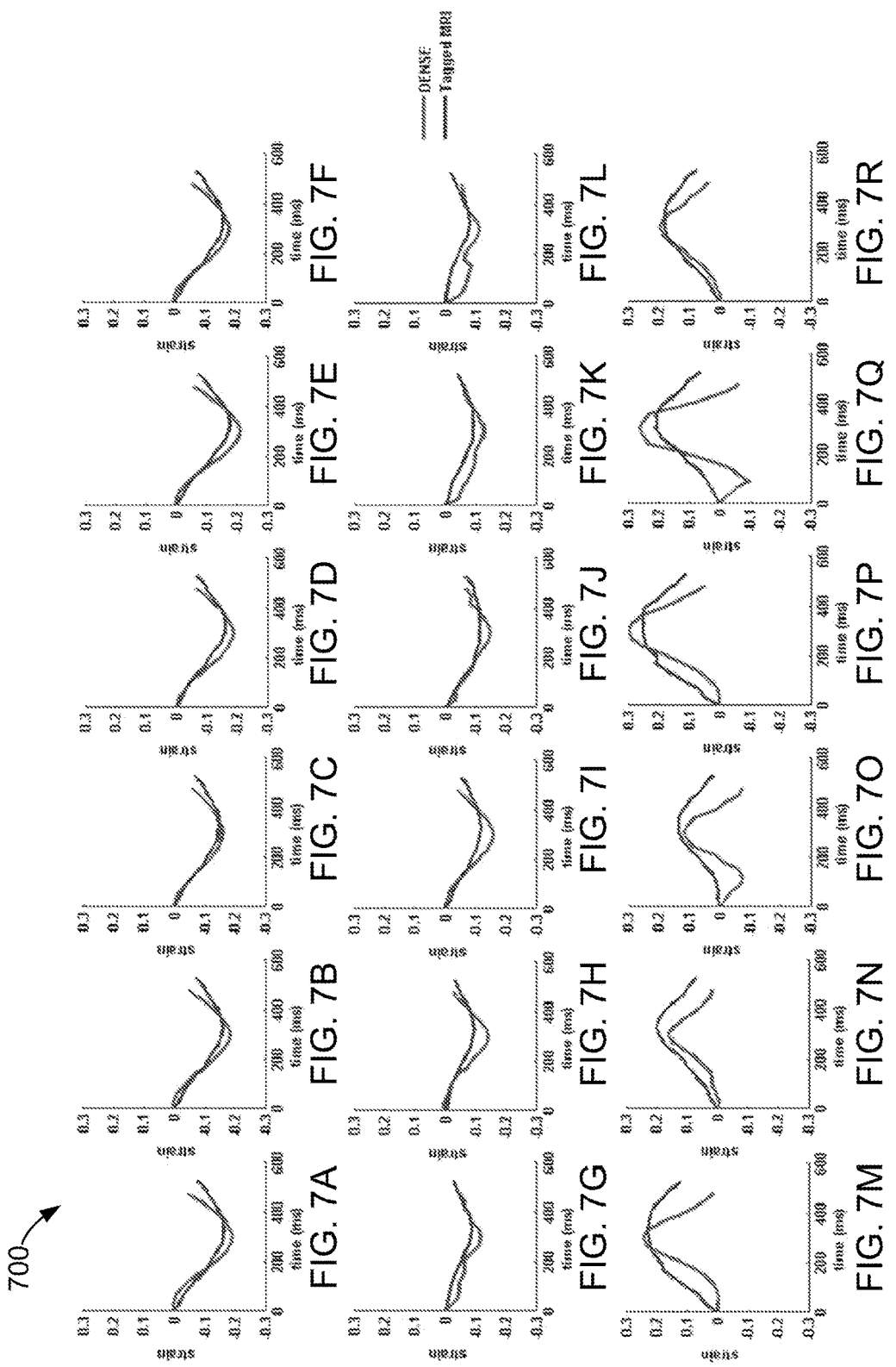

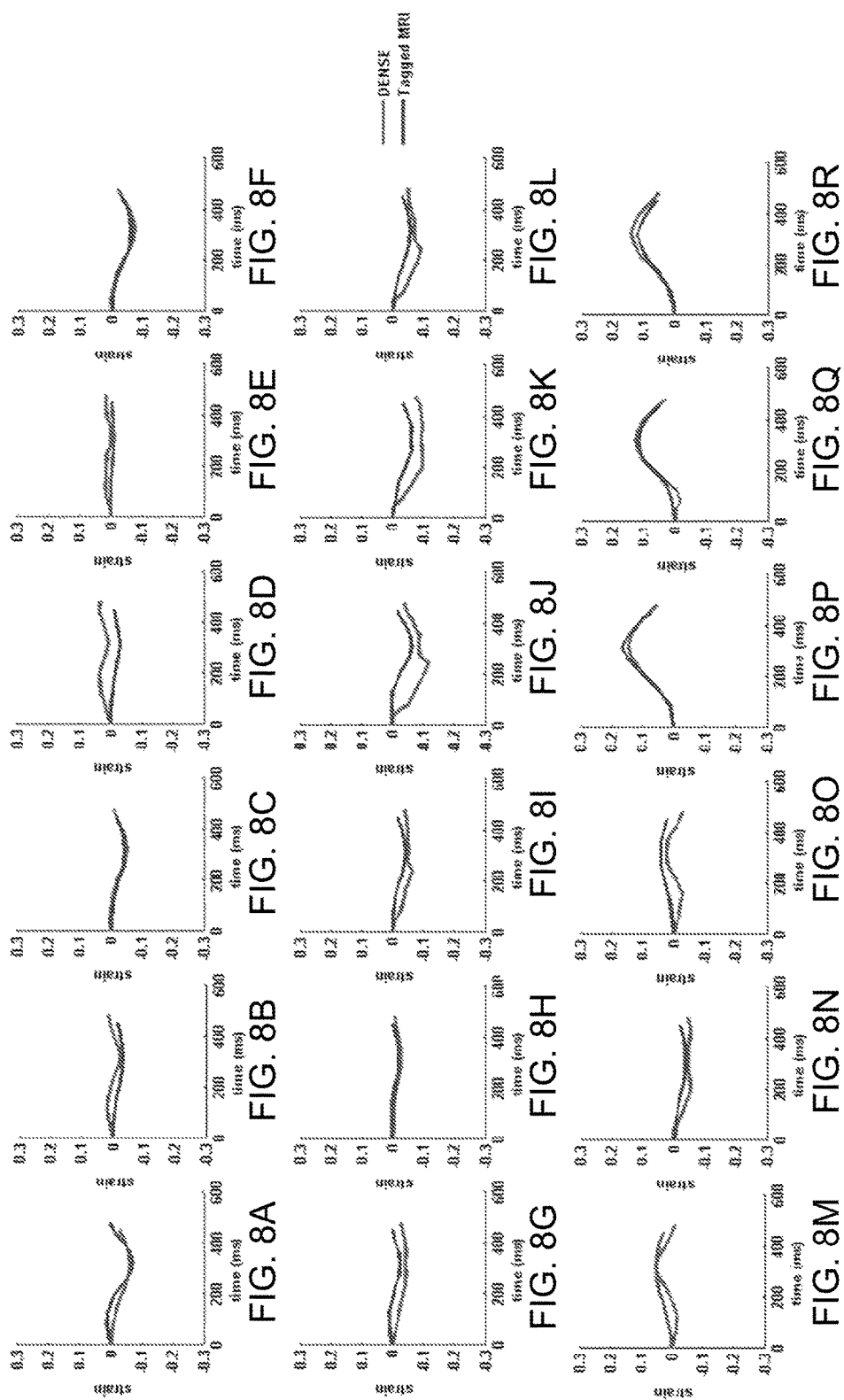

| Region | Circ. | Long. | Rad. | Twist (°) | Tors. (°) |
|---|---|---|---|---|---|
| Anteroseptal-basal | -0.14 ± 0.05 | -0.13 ± 0.06 | 0.19 ± 0.10 | -13.1 ± 8.3 | -- |
| Anterior-basal | -0.14 ± 0.05 | -0.13 ± 0.04 | 0.19 ± 0.10 | -10.2 ± 6.1 | -- |
| Anterolateral-basal | -0.15 ± 0.03 | -0.15 ± 0.04 | 0.19 ± 0.13 | -10.2 ± 7.3 | -- |
| Posterolateral-basal | -0.15 ± 0.06 | -0.16 ± 0.05 | 0.24 ± 0.13 | -14.1 ± 8.2 | -- |
| Posterior-basal | -0.12 ± 0.05 | -0.16 ± 0.05 | 0.23 ± 0.12 | -11.5 ± 7.0 | -- |
| Posterorseptal-basal | -0.11 ± 0.05 | -0.14 ± 0.05 | 0.18 ± 0.12 | -12.3 ± 10.2 | -- |
| Anteroseptal-midLV | -0.13 ± 0.05 | -0.13 ± 0.06 | 0.20 ± 0.12 | 10.9 ± 8.1 | 14.4 ± 5.5 |
| Anterior-midLV | -0.14 ± 0.05 | -0.12 ± 0.05 | 0.17 ± 0.07 | 12.9 ± 7.7 | 13.8 ± 6.2 |
| Anterolateral-midLV | -0.18 ± 0.04 | -0.14 ± 0.04 | 0.22 ± 0.12 | 8.5 ± 7.7 | 11.3 ± 5.0 |
| Posterolateral-midLV | -0.20 ± 0.07 | -0.15 ± 0.04 | 0.24 ± 0.12 | 7.5 ± 8.9 | 13.0 ± 6.6 |
| Posterior-midLV | -0.16 ± 0.05 | -0.15 ± 0.04 | 0.21 ± 0.10 | 9.5 ± 10.7 | 12.6 ± 6.7 |
| Posterorseptal-midLV | -0.14 ± 0.06 | -0.13 ± 0.05 | 0.20 ± 0.12 | 16.5 ± 9.7 | 15.2 ± 7.6 |
| Septal-apex | -0.15 ± 0.07 | -0.12 ± 0.06 | 0.17 ± 0.09 | 13.7 ± 6.1 | 7.9 ± 3.8 |
| Anterior-apex | -0.16 ± 0.07 | -0.10 ± 0.06 | 0.20 ± 0.09 | 15.2 ± 4.7 | 7.8 ± 2.6 |
| Lateral-apex | -0.21 ± 0.07 | -0.12 ± 0.04 | 0.22 ± 0.12 | 8.1 ± 7.2 | 6.1 ± 3.6 |
| Posterior-apex | -0.17 ± 0.04 | -0.13 ± 0.04 | 0.17 ± 0.11 | 17.3 ± 12.9 | 8.6 ± 3.9 |

| Region | Circ. | Long. | Rad. | Twist (°) | Tors. (°) |
|---|---|---|---|---|---|
| Anteroseptal-basal | -0.04 ± 0.06 | 0.03 ± 0.04 | 0.01 ± 0.05 | 0.4 ± 1.7 | -- |
| Anterior-basal | -0.14 ± 0.04 | -0.01 ± 0.05 | 0.05 ± 0.04 | 2.1 ± 0.7 | -- |
| Anterolateral-basal | -0.10 ± 0.03 | -0.07 ± 0.03 | 0.10 ± 0.05 | 3.7 ± 1.1 | -- |
| Posterolateral-basal | -0.09 ± 0.01 | -0.02 ± 0.03 | 0.07 ± 0.03 | 2.2 ± 1.3 | -- |
| Posterior-basal | -0.02 ± 0.05 | 0.03 ± 0.04 | 0.05 ± 0.04 | 0.4 ± 0.9 | -- |
| Posteroseptal-basal | -0.02 ± 0.08 | 0.03 ± 0.06 | -0.01 ± 0.03 | 1.1 ± 1.7 | -- |
| Anteroseptal-midLV | -0.09 ± 0.07 | -0.01 ± 0.01 | 0.01 ± 0.04 | -0.4 ± 0.8 | -0.3 ± 0.6 |
| Anterior-midLV | -0.03 ± 0.04 | -0.05 ± 0.03 | 0.05 ± 0.04 | 1.7 ± 0.5 | -0.2 ± 0.1 |
| Anterolateral-midLV | -0.10 ± 0.02 | -0.06 ± 0.02 | 0.09 ± 0.04 | 2.2 ± 0.7 | -0.6 ± 0.2 |
| Posterolateral-midLV | -0.09 ± 0.03 | -0.03 ± 0.01 | 0.06 ± 0.03 | 1.4 ± 1.2 | -0.4 ± 0.1 |
| Posterior-midLV | -0.02 ± 0.06 | 0.00 ± 0.01 | 0.04 ± 0.05 | 0.8 ± 0.7 | 0.2 ± 0.1 |
| Posteroseptal-midLV | -0.02 ± 0.08 | 0.01 ± 0.03 | -0.02 ± 0.03 | 0.3 ± 0.8 | -0.3 ± 0.6 |
| Septal-apex | -0.09 ± 0.08 | -0.02 ± 0.02 | 0.01 ± 0.03 | 0.1 ± 0.4 | -0.2 ± 0.6 |
| Anterior-apex | -0.15 ± 0.04 | -0.07 ± 0.03 | 0.04 ± 0.02 | 1.6 ± 0.3 | -0.2 ± 0.2 |
| Lateral-apex | -0.10 ± 0.03 | -0.07 ± 0.02 | 0.06 ± 0.03 | 0.1 ± 0.9 | -0.9 ± 0.1 |
| Posterior-apex | -0.02 ± 0.06 | -0.03 ± 0.03 | 0.05 ± 0.05 | 1.0 ± 0.6 | 0.2 ± 0.1 |

FIG. 10

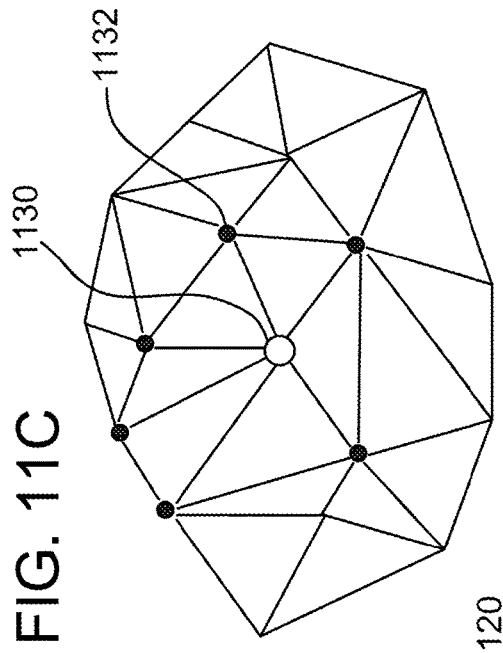
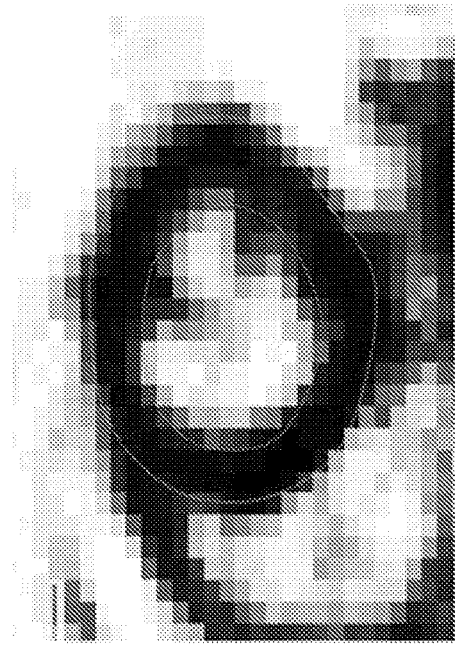
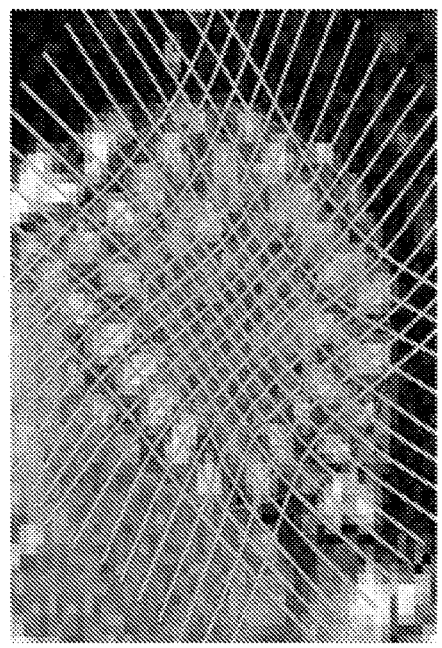

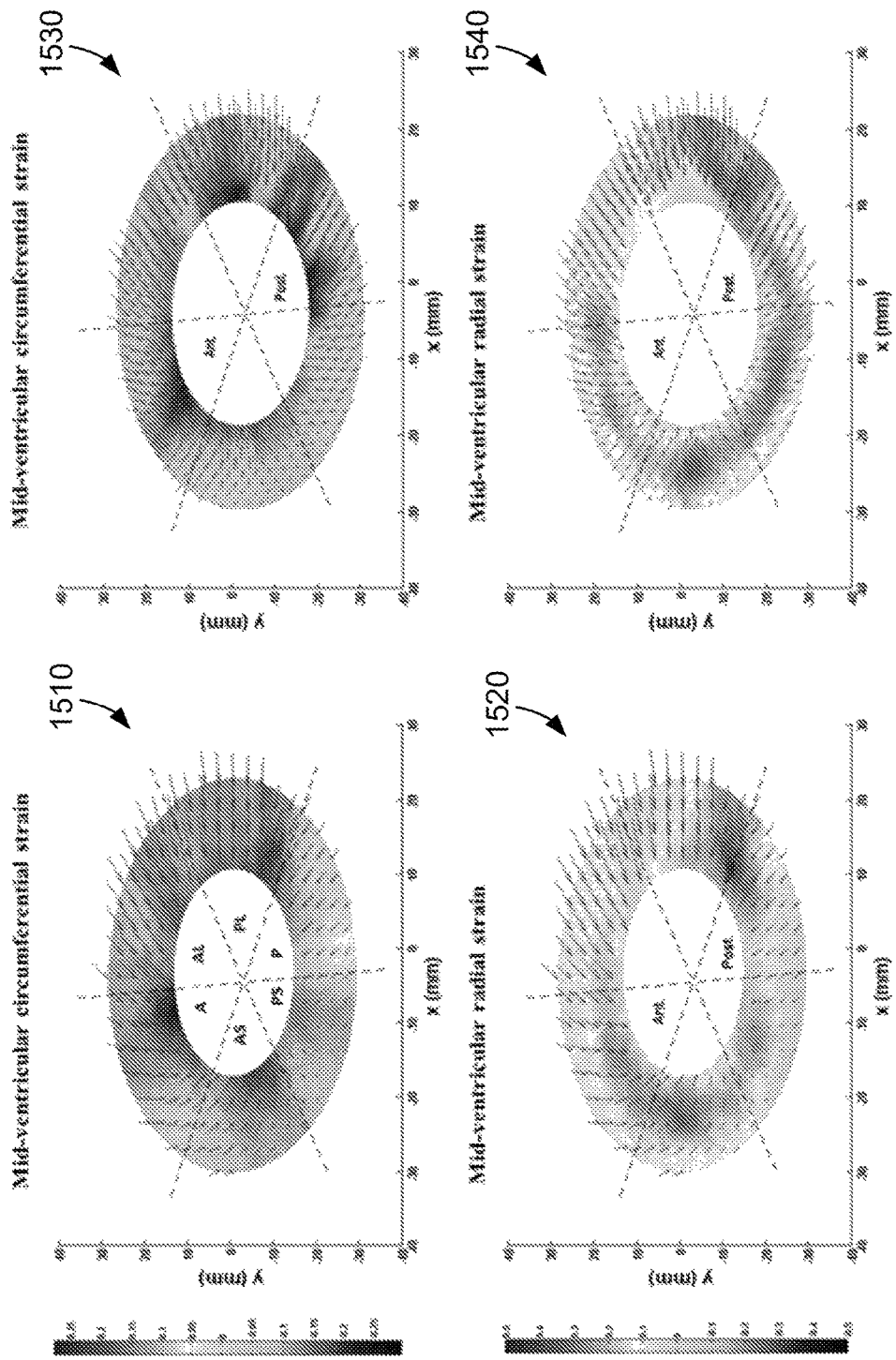

| Strains | Anterior | Antero-lateral | Postero-lateral | Posterior | Postero-septal | Antero-septal |
|---|---|---|---|---|---|---|
| (a) TMRI | | | | | | |
| Circumferential | | | | | | |
| Apical | -0.17 ± 0.04 | -0.19 ± 0.02 | | -0.16 ± 0.03 | -0.14 ± 0.04 | -0.14 ± 0.03 |
| Mid-ventricular | -0.13 ± 0.03 | -0.16 ± 0.03 | -0.18 ± 0.03 | -0.18 ± 0.04 | -0.14 ± 0.03 | -0.15 ± 0.03 |
| Basal | -0.16 ± 0.04 | -0.17 ± 0.03 | -0.18 ± 0.04 | -0.16 ± 0.04 | -0.15 ± 0.03 | |
| Radial | | | | | | |
| Apical | 0.13 ± 0.08 | 0.15 ± 0.06 | | 0.15 ± 0.09 | 0.15 ± 0.09 | 0.18 ± 0.13 |
| Mid-ventricular | 0.14 ± 0.10 | 0.13 ± 0.10 | 0.25 ± 0.17 | 0.15 ± 0.12 | 0.21 ± 0.14 | 0.15 ± 0.07 |
| Basal | 0.12 ± 0.08 | 0.21 ± 0.11 | 0.24 ± 0.12 | 0.19 ± 0.10 | 0.17 ± 0.09 | |
| DENSE | | | | | | |
| Circumferential | | | | | | |
| Apical | -0.18 ± 0.03 | -0.20 ± 0.02 | | -0.15 ± 0.04 | -0.16 ± 0.05 | -0.18 ± 0.04 |
| Mid-ventricular | -0.17 ± 0.04 | -0.19 ± 0.04 | -0.20 ± 0.03 | -0.14 ± 0.04 | -0.14 ± 0.04 | -0.16 ± 0.05 |
| Basal | -0.15 ± 0.05 | -0.18 ± 0.05 | -0.19 ± 0.03 | -0.14 ± 0.03 | -0.15 ± 0.05 | |
| Radial | | | | | | |
| Apical | 0.13 ± 0.08 | 0.21 ± 0.14 | | 0.13 ± 0.11 | 0.16 ± 0.10 | 0.20 ± 0.14 |
| Mid-ventricular | 0.17 ± 0.08 | 0.16 ± 0.09 | 0.24 ± 0.11 | 0.18 ± 0.10 | 0.17 ± 0.10 | 0.15 ± 0.11 |
| Basal | 0.09 ± 0.07 | 0.25 ± 0.16 | 0.32 ± 0.09 | 0.17 ± 0.10 | 0.15 ± 0.12 | |
| (B) Study-1 | | | | | | |
| Circumferential | | | | | | |
| Apical | -0.20 ± 0.04 | -0.23 ± 0.04 | | -0.19 ± 0.03 | -0.19 ± 0.03 | -0.18 ± 0.03 |
| Mid-ventricular | -0.19 ± 0.04 | -0.20 ± 0.05 | -0.20 ± 0.03 | -0.16 ± 0.05 | -0.18 ± 0.04 | -0.14 ± 0.04 |
| Basal | -0.16 ± 0.04 | -0.15 ± 0.05 | -0.18 ± 0.03 | -0.13 ± 0.05 | -0.16 ± 0.04 | |
| Radial | | | | | | |
| Apical | 0.13 ± 0.08 | 0.27 ± 0.15 | | 0.17 ± 0.10 | 0.23 ± 0.11 | 0.20 ± 0.09 |
| Mid-ventricular | 0.14 ± 0.06 | 0.24 ± 0.10 | 0.32 ± 0.11 | 0.22 ± 0.09 | 0.22 ± 0.09 | 0.16 ± 0.09 |
| Basal | 0.10 ± 0.07 | 0.22 ± 0.17 | 0.36 ± 0.17 | 0.18 ± 0.11 | 0.20 ± 0.10 | |
| Study-2 | | | | | | |
| Circumferential | | | | | | |
| Apical | -0.21 ± 0.04 | -0.23 ± 0.04 | | -0.20 ± 0.05 | -0.21 ± 0.03 | -0.17 ± 0.03 |
| Mid-ventricular | -0.18 ± 0.03 | -0.19 ± 0.04 | -0.19 ± 0.03 | -0.14 ± 0.04 | -0.17 ± 0.03 | -0.15 ± 0.04 |
| Basal | -0.17 ± 0.05 | -0.16 ± 0.05 | -0.17 ± 0.03 | -0.13 ± 0.04 | -0.15 ± 0.03 | |
| Radial | | | | | | |
| Apical | 0.15 ± 0.10 | 0.25 ± 0.17 | | 0.15 ± 0.11 | 0.23 ± 0.16 | 0.22 ± 0.12 |
| Mid-ventricular | 0.13 ± 0.10 | 0.21 ± 0.10 | 0.29 ± 0.09 | 0.18 ± 0.09 | 0.22 ± 0.09 | 0.15 ± 0.09 |
| Basal | 0.07 ± 0.07 | 0.20 ± 0.17 | 0.30 ± 0.11 | 0.23 ± 0.06 | 0.19 ± 0.11 | |

SYSTEMS AND METHODS FOR MEASURING CARDIAC STRAIN

ACKNOWLEDGEMENT OF GOVERNMENT SUPPORT

This invention was made with government support under grant HL112804awarded by the National Institutes of Health. The government has certain rights in the invention.

BACKGROUND

The field of the invention relates generally to Magnetic Resonance Imaging (MRI) of regional myocardial function, and more specifically, to a meshfree numerical analysis technique for rapid computation of strain from MRI images acquired with a DENSE sequence.

Magnetic Resonance Imaging (MRI) is considered a viable noninvasive technology for visualizing regional myocardial function. MRI is characterized by higher spatial and temporal resolution than echocardiography. The higher resolution facilitates detailed quantitative assessment of cardiac wall motion and computation of transmural strains. Myocardial contractility (i.e., strain) is an important metric for quantifying myocardial dysfunction in patients.

Imaging techniques such as tagged MRI (TMRI) including post-processing algorithms are commonly used to visualize regional myocardial function. TMRI uses pulse sequences to create temporary features, or 'tags', that follow the motion of the myocardium. By tracking the motion of the tags through the various stages of the cardiac cycle, displacement information is obtained and processed through techniques to provide additional information regarding the myocardium, such as strain.

However, TMRI has a relatively low spatiotemporal resolution in comparison to other MRI techniques. A low spatiotemporal resolution can result in imprecise data used in the post-processing algorithms for strain analysis. In addition, the post-processing methods used in TMRI have long processing times, creating a potential inconvenience to the operator and the subject that can increase the duration of the MRI operation.

BRIEF SUMMARY OF THE DESCRIPTION

In one aspect, a method for performing three-dimensional cardiac strain analysis is provided. The method includes acquiring magnetic resonance imaging (MRI) data using a Displacement ENcoding with Stimulated Echoes (DENSE) sequence, segmenting the acquired MRI data, performing phase unwrapping on the segmented MRI data to obtain displacement data, and performing strain analysis on the displacement data using a meshfree numerical analysis technique.

In another aspect, a controller coupled to an MRI device for performing three-dimensional cardiac strain analysis is provided. The controller includes a processor and a memory device. The memory device includes instructions executable by the processor to cause the controller to acquire MRI data from the MRI device using a DENSE sequence, segment the acquired MRI data, perform phase unwrapping on the segmented MRI data to obtain displacement data, and perform strain analysis on the displacement data using a meshfree numerical analysis technique.

In yet another aspect, an MRI system for performing three-dimensional cardiac strain analysis is provided. The system includes an MRI device configured to generate MRI data and a controller coupled to the MRI device. The controller includes a processor and a memory device. The memory device includes instructions executable by the processor to cause the controller to acquire the MRI data from the MRI device using a DENSE sequence, segment the acquired MRI data, perform phase unwrapping on the segmented MRI data to obtain displacement data, and perform strain analysis on the displacement data using a meshfree numerical analysis technique.

BRIEF DESCRIPTION OF THE DRAWINGS

FIG. 1A shows uninterpolated deformed tag lines in tagged MRI using a semi-automated tag-finding algorithm.

FIG. 1B is a flood-filled quality image used in DENSE to find displacement vectors.

FIG. 1C shows the unwrapped phases of FIG. 1b in the vertical orientation.

FIG. 1D shows the unwrapped phases of FIG. 1b in the horizontal orientation.

FIG. 1E shows the unwrapped phases of FIG. 1b in the longitudinal orientation.

FIG. 1F is an example demonstrating how rotation, α, in opposite directions creates a torsion angle $\theta_T$.

FIG. 6A shows systolic endocardial and epicardial circumferential strain estimated with DENSE-RPIM in DCM patients.

FIG. 6B shows systolic endocardial and epicardial longitudinal strain estimated with DENSE-RPIM in DCM patients.

FIG. 6C shows systolic endocardial and epicardial radial strain estimated with DENSE-RPIM in DCM patients.

FIGS. 7A-R are strain versus time plots for sixteen AHA recommended LV segments from a healthy subject in circumferential (FIGS. 7a-f), longitudinal (FIGS. 7g-l), and radial (FIGS. 7m-r) strains in the DENSE-TMRI study.

FIGS. 8A-R are strain versus time plots for sixteen AHA recommended LV segments from a DCM patient in circumferential (FIGS. 8a-f), longitudinal (FIGS. 8g-l), and radial (FIGS. 8m-r) strains in the DENSE-TMRI study.

FIG. 9 is a table of regional strain, twist angles, and torsion angles in healthy subjects found using DENSE-RPIM in the AHA-recommended sixteen segments.

FIG. 10 is a table of regional strain, twist angles, and torsion angles in DCM patients found using DENSE-RPIM in the AHA-recommended sixteen segments.

FIG. 11A is a flood-filled quality image used in DENSE to find displacement of the myocardium.

FIG. 11B shows deformed tag lines used in TMRI to track displacement.

FIG. 11C is a conceptual example of NNFEM for constructing shape functions from a quadrature point (red) and neighbors (blue).

FIG. 15A shows NNFEM simulated mid-ventricular systolic circumferential and radial strains estimated with DENSE displacements, with displacement vectors in red.

FIG. 15B shows NNFEM simulated mid-ventricular systolic circumferential and radial strains estimated with TMRI displacements, with displacement vectors in red.

FIG. 16A shows NNFEM simulated basal systolic circumferential and radial strains estimated with DENSE in the subject of FIG. 15a.

FIG. 16B shows NNFEM simulated apical systolic circumferential and radial strains estimated with DENSE in the subject of FIG. 15a.

FIG. 17A is a table of the regional circumferential and radial strains calculated from DENSE-TMRI comparison studies.

FIG. 17B is a table of the regional circumferential and radial strains calculated from DENSE repeatability studies.

DETAILED DESCRIPTION

Figure 2:
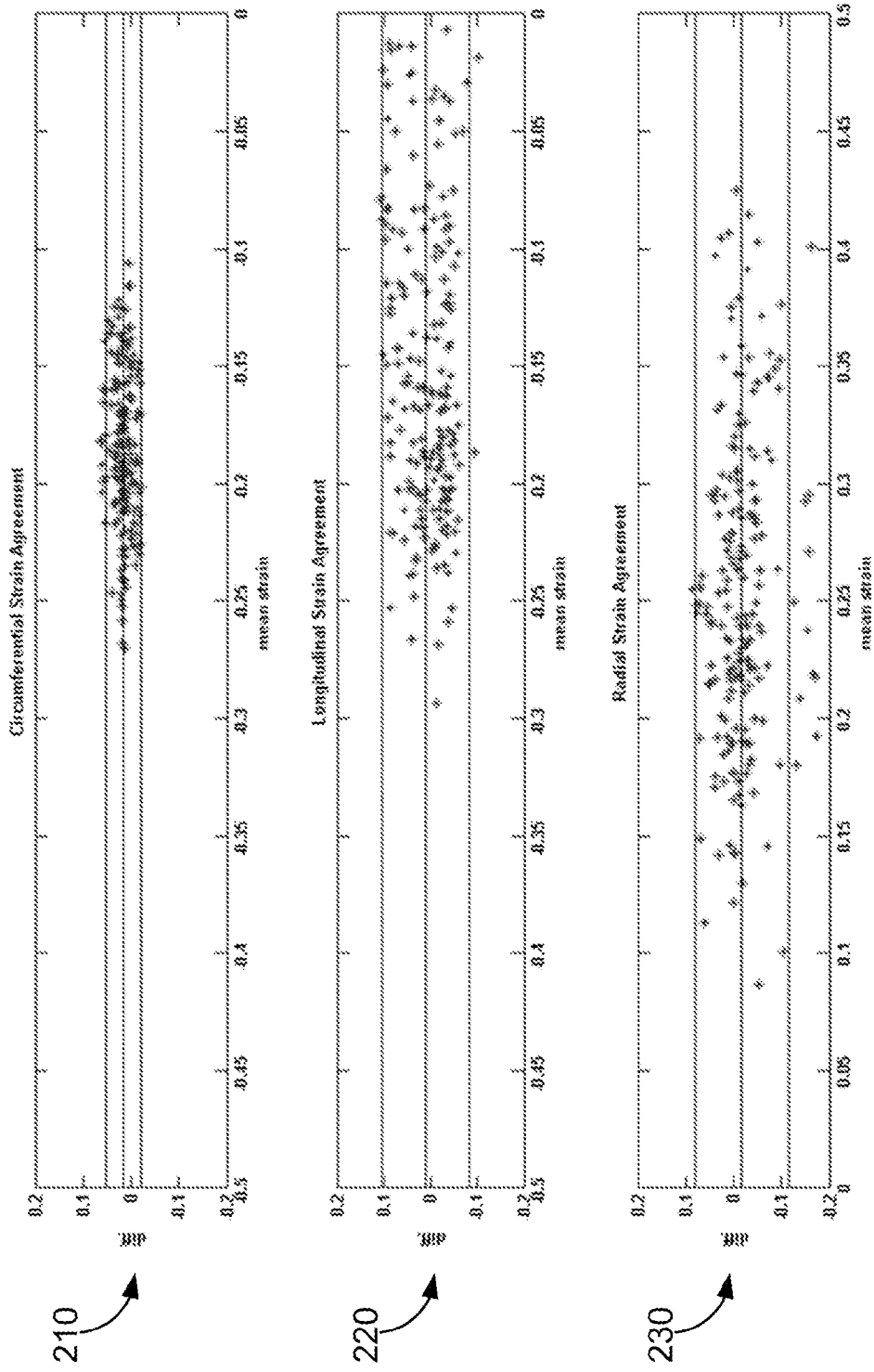
FIG. 2 is three Bland-Altman plots of the circumferential, longitudinal, and radial strain calculated in a DENSE-TMRI study of healthy subjects.

Systems and methods are provided herein for analyzing myocardial contractility using displacement-encoded MRI techniques. MRI data collected from an MRI device is encoded with phase information. The phase information is associated with displacement data of a myocardium. The MRI data is segmented to focus on a region of the myocardium. The phase information is "unwrapped" from a $2\pi$ interval to decode the displacement data for analysis. Based on the displacement data, cardiac strain analysis is performed. Cardiac strain analysis facilitates identification of myocardium health issues and understanding of myocardium operation. The systems and methods described herein are configured to reduce the time taken to collect and process MRI data from a patient to facilitate reduced operation time.

An MRI technique known as Displacement ENcoding with Stimulated Echoes (DENSE) was developed that directly encodes tissue displacement in the phases of complex images and enables direct determination of regional myocardial function. Cine DENSE is characterized by high spatiotemporal resolution, relative to some known techniques such as TMRI. Cine refers to a set of temporal images that may be used to display the motion of an item. In the heart, the motion being displayed is typically the motion of a wall of the heart. In one example, cineradiography records 30 frames per second fluoroscopic images of the heart taken during injection of a dye to contrast the myocardium for clear images. Cine DENSE provides a time series of myocardial displacements using three dimensional (3D) quality-guided spatiotemporal phase unwrapping. In other embodiments, alternative DENSE techniques such as non-free-breathing DENSE are implemented.

To complement the high spatiotemporal resolution of DENSE, a fast post-processing algorithm to display regional myocardial function and provide strain analysis is desirable. A post-processing technique centered on a radial point interpolation method (RPIM) described further below is implemented to provide fast, reliable, and accurate results.

Computation of specific mechanical parameters, segmentation of the myocardium, and phase unwrapping in DENSE is accomplished with a custom software utility implemented in C++. In other embodiments the custom software utility is implemented in a different programming language.

Cine DENSE data is acquired with displacement encoding applied in two orthogonal in-plane directions and one through plane direction and a four channel body phased array radiofrequency (RF) coil is used for receiving signals. Typical imaging parameters include field of view (FOV) of 359×269 mm, echo train length (ETL) of 1, echo time (TE) of 8 ms, repetition time (TR) of 32.5 ms, matrix size of 112×84 pixels with 2.81 mm pixel size, 8 mm slice thickness and 12 to 21 cardiac phases using an echo planar imaging (EPI) cine DENSE sequence. Other embodiments using alternative DENSE techniques use typical imaging parameters known to those of ordinary skill in the art.

The American Heart Association (AHA) sets guidelines for segmenting the myocardium for clinical and research purposes. The myocardium is segmented using a semi-automated method where manual delineation of the endocardial and epicardial contours are performed at the initial cardiac phase, followed by propagation of these contours to all other cardiac phases. In an example study described below, the segmentation process generated sixteen regions for strain measurements within the left ventricle (LV) in accordance with AHA guidelines. In other embodiments, the DENSE-RPIM method is used for regional strain analysis in the left atrium, right atrium, or right ventricle.

Finding DENSE displacements by phase unwrapping consists of computing and averaging phase angles of a series of Fourier transforms in an image by a method of suppressing unwanted environmental effects such as respiration-induced artifacts imposed on the image resolution. The computed phase angles inherently contain ambiguities of integral multiples of $2\pi$ where it is important to obtain continuous phase curves. The spatiotemporal phase unwrapping algorithm implemented in the example embodiment includes phase unwrapping along an integral path by integrating the phase differences between local phases which is assisted by a flood-fill quality guided algorithm. Temporal fitting in each encoding direction is achieved with fitting displacement data from consecutive phases with periodic (Fourier series) basis functions and coefficients found using discrete Fourier transform of the cine DENSE data.

FIG. 1A depicts uninterpolated deformed tag lines 110 used in TMRI in end-systole in a healthy subject. FIG. 1B is a flood-filled quality image 120 used to find DENSE displacements in the subject of FIG. 1A. FIGS. 1C, 1D, and 1E are unwrapped smooth phases 130, 140, 150 within the myocardium in vertical, horizontal and longitudinal orientations, respectively, in the subject of FIG. 1A.

Strain analysis performed using the high spatiotemporal resolution displacement data from DENSE and a customized RPIM algorithm described herein may provide accurate, reliable, and fast results. The RPIM algorithm is implemented using MATLAB (Mathworks Inc., Natick, Mass.) in the example study described below. In other embodiments, the RPIM algorithm may be implemented in a different application or applications.

The method of transformation of 2D endocardial and epicardial boundaries, displacements vectors and other landmarks from the MRI images described below into global 3D space is accomplished using a 4D Euclidean transformation, expressed as:

$$\begin{bmatrix} x_{3D} \\ y_{3D} \\ z_{3D} \\ 1 \end{bmatrix} = \begin{bmatrix} c_x & r_x & n_x & t_x \\ c_y & r_y & n_y & t_y \\ c_z & r_z & n_y & t_y \\ 0 & 0 & 0 & 1 \end{bmatrix} \begin{bmatrix} x_{2D} \\ y_{2D} \\ 0 \\ 1 \end{bmatrix} \quad (1)$$

where $(x, y, z)_{3D}$ and $(x, y)_{2D}$ are the spatial coordinates, $c_{x,y,z}$ and $r_{x,y,z}$ are unit column and row vectors to an imaging plane, $n_{x,y,z}$ is a normal vector to the imaging plane, and $t_{x,y,z}$ is a translation vector corresponding to the origin of the imaging plane.

RPIM is a meshfree numerical analysis method for multidimensional strain analysis within a continuum where a set of nodes neighboring a point of integration (quadrature point) are selected for shape function constructions. The RPIM method is briefly described in the following.

A continuous displacement field function, u(x), passing through a group of scattered nodes, x, obtained from the cine DENSE MRI technique, within a domain is expressed as:

$$u(x) = \Sigma_{i=1}^n B_i(x)a_i + \Sigma_{k=1}^m p_k(x)b_k \quad (2)$$

and is represented in matrix form by:

$$u(x) = B^T(x)a + P^T(x)b \quad (3)$$

where P(x) is a matrix of monomial bases and b is a vector of coefficients to which radial basis functions (RBF) B(x) with a as the coefficient vector, are added. The second component of Equation 2 passed through each scattered node point $x_k$ to generate a polynomial function. $B(x)^{-1}$ exists for arbitrary scattered nodes, and is an advantage of radial basis over using only polynomial bases.

The RBF used in the example embodiment, $B_i$, is a multiquadric (MQ) type of RBF, and is expressed as:

$$B_i(x,y,z) = (r_i^2 + R)^q, r_i = r(x_i, y_i, z_i) \quad (4)$$

where $r_i$ is the distance between point $x_i$ and node x. R and q are shape parameters generally determined by numerical trials or values recommended in the art. In other embodiments, the RBF implemented is an alternative type. In this case, previous literature demonstrates that q values less than 1 and R values of approximately 1.0-2.0 produce well-conditioned results as known within the art.

RBFs have advantages over polynomial functions and finite element methods, including: (i) approximation functions passing through each node point in the influence domain; and (ii) shape functions and derivatives with an arbitrary distribution of nodes may be easily developed. Continuously differentiable and integrable MQ type RBFs provide element-free schemes of approximation with individual patient-specific strain grid points undergoing strain computation from phase unwrapped displacements in DENSE and original and interpolated tagged data in TMRI. Furthermore, RPIM also enables computation of temporal strain trajectories for both sequences for all phases between and including end-diastole and end-systole.

With the introduction of RBFs, additional polynomial terms can be added without the risk of singularities. Additionally, the displacement field function is constrained, the constraint is expressed as:

$$u(x) = \Sigma_{i=1}^n p_i(x_k)a_i = 0 \text{ with } k=1 \ldots m \quad (5)$$

where $p_k(x)$ are linear monomial terms with the limit m≪n.

Equation 2 and Equation 4 may be assembled into a point-wise global basis function, $G_0$, expressed as:

$$\begin{bmatrix} B_0 & P \\ P^T & 0 \end{bmatrix} \begin{bmatrix} a \\ b \end{bmatrix} = G_0 \begin{bmatrix} a \\ b \end{bmatrix} = \begin{bmatrix} u_e \\ 0 \end{bmatrix} \quad (6)$$

with $u_e = [u_1, u_2, \ldots u_n]$.

The interpolation displacement field function may then be expressed as:

$$u(x) = [B_1(x), B_2(x), \ldots, B_n(x), p_1(x), p_2(x), \ldots p_m(x)]$$
$$[a_1, a_2, \ldots, a_n, b_1, b_2, \ldots, b_m]^T \quad (7)$$

When complete k order polynomial terms are included in the basis, a k order polynomial can be reproduced. Thus, including polynomial terms in the basis can be expected to obtain good approximation accuracy. The function in Equation 6 can then be used to define the strain deformation tensor, F, expressed as:

$$F = \frac{\partial u(x)}{\partial \alpha} = \frac{\partial [B(x), P(x)]}{\partial x} [a, b]^T \quad \alpha = x, y, z \quad (8)$$

A 3D finite Lagrange strain tensor, E, is computed from F The equation for the Lagrange strain tensor E is expressed as:

$$E = \frac{1}{2}(F^T F - I) \quad (9)$$

where I is the identity matrix.

In the example embodiment, a point-wise Multi-Parametric (strain) Z-Score (MPZS) such as Equation 10 is calculated to provide a statistical value that compares strain in one patient to past or average strain of previous patients and simulations. MPZS is expressed as $$MPZS = \frac{1}{4}\left(-\frac{\varepsilon_r - \mu_{n,r}}{\sigma_{n,r}} + \frac{\varepsilon_c - \mu_{n,c}}{\sigma_{n,c}} + \frac{\varepsilon_l - \mu_{n,l}}{\sigma_{n,l}} + \frac{\varepsilon_{cl} - \mu_{n,cl}}{\sigma_{n,cl}}\right) \quad (10)$$

where ε is the patient-specific strain, $\mu_n$ is the averaged normal strain, and $\sigma_n$ is standard deviation from the normal strains database. The subscript r is radial, c is circumferential, l is longitudinal, cl is circumferential-longitudinal and n represents average. As used herein, the MPZS may also be represented as P. In some embodiments, shear measurements are not included in multiparametric strain calculations such as the MPZS calculations.

In the example embodiment, a twist or rotation) angle is identified for two slices to calculate a torsion angle $\theta_T$. FIG. 1F depicts a diagram 160 of a rotation of basal slice and an apex slice around an axis of rotation AR. Angles of rotations $\alpha_{BASE}$ and $\alpha_{APEX}$ are used to calculate the torsion angle $\theta_T$ of a region. In the example embodiment, the torsion angle $\theta_T$ is computed as the angle between the directions of end-diastolic radial and circumferential strains in successive cardiac phases measured from the axis of rotation AR. A positive twist is defined as counterclockwise rotation when viewed from the LV apex. Three dimensional torsion angles $\theta_T$ or global approximations of circumferential longitudinal shear angles are computed from the differences in apical and basal rotation angles, multiplied by the ratio of average LV radius and LV length. The axis of rotation for 3D torsion angles $\theta_T$ is computed from the 3D centers of each short-axis slice, which approximated to the line between the most apical and basal slices. The equation for estimating torsion, $\alpha_T$, is expressed as:

$$\alpha_T = (\theta_A - \theta_B)\frac{R_M}{L} \qquad (11)$$

where $\theta_A$ and $\theta_B$ are the apical and basal rotation angles respectively, $R_M$ is the average radius and L is the length of the LV.

The example study was conducted using the DENSE-RPIM method of the example embodiment. The example study compares the strain analysis of the DENSE-RPIM method to TMRI as well as the repeatability, or reliability, of the proposed DENSE-RPIM method. Twelve healthy subjects were imaged in a 1.5 Tesla (T) Avanto (Siemens, Erlangen, Germany) MRI device for the DENSE-TMRI comparison and ten healthy subjects (i.e., without known myocardium issues) were imaged in the DENSE-RPIM repeatability study. The average age of the twenty-two healthy subjects was 45.9±13.8 years and the average mass was 73.4±13.4 kg. Six subjects with non-ischemic, non-valvular dilated cardiomyopathy (DCM) were included in the DENSE-TMRI comparison with an average age of 60.3±13.1 years and an average mass of 93.4±21.6 kg. The male to female recruitment ratio of the DCM patients was 5:1.

All healthy subjects were recruited without exclusions based on age, sex or ethnicity, or racial background. Six female and six male subjects were recruited for the comparison study and six females and four males recruited for the repeatability study. Subjects for the repeatability study were removed from the scanner after the first scan and repositioned in approximately the same position during the second scan held on the same day. The criteria for recruiting DCM patients were based on diagnosis of heart failure which included New York Heart Association (NYHA) heart failure class ranging II-ID and LV ejection fraction (LVEF) less than 35%. Heart rates (HR) and blood pressures (BP) were recorded in both healthy subjects and in DCM patients.

In the comparison of DENSE-RPIM and TMRI, the processing duration was evaluated. The time taken for segmentation and combined displacement-strain analysis between reference and deformed timeframes was measured for both methods.

The signal-to-noise ratio (SNR) was calculated to provide an indication of measurement accuracy of the collected data. SNR was computed by averaging the signal in a region of interest (ROI) in an image and sampling from an ROI of background air pixels. The background region should not be placed over artifacts. SNR (dimensionless) is expressed as:

$$SNR = 0.655 \frac{S}{SD_{air}} \qquad (12)$$

where S is the mean signal in the image ROI, and $SD_{air}$ is the standard deviation from the background air ROI. The correction factor of 0.655 is due to background noises in magnitude images that tend toward a Rayleigh distribution as SNR goes to zero. Three magnitude images (basal, mid-ventricular, and apical sections) in three orthogonal directions (total of nine) from each subject's earliest and latest phases were used for SNR analysis.

Bland-Altman statistical analyses were used for establishing agreement between DENSE-RPIM and TMRI as well as the repeatability study. For regional Bland-Altman analysis, measurements were taken from six regions in each of the basal and mid-ventricular levels and four from the apex making it a total of sixteen regions per subject according to AHA recommended segmentations guidelines as described above. Paired Student's t-tests were additionally used to investigate the likelihood of similar mean strains between DENSE-RPIM and TMRI and in the repeatability study.

Average HR monitored in healthy subjects was 68.0±8.1 bpm and average BP was 128.4±18.7/79.7±13.1 mmHg from the DENSE-TMRI comparison study. Average HR monitored during the repeatability study was 68.7±7.2 bpm and average BP was 124.3±11.2/76.5±7.3 mmHg Average HR monitored in DCM patients was 75.9±10.5 bpm and average BP was 117.7±9.8/72.3±8.8 mmHg SNR computed from DENSE magnitude images were 35±9 and 29±4 at earliest and latest cardiac phases in healthy subjects and 26±9 and 24±5 in DCM patients.

Figure 3:
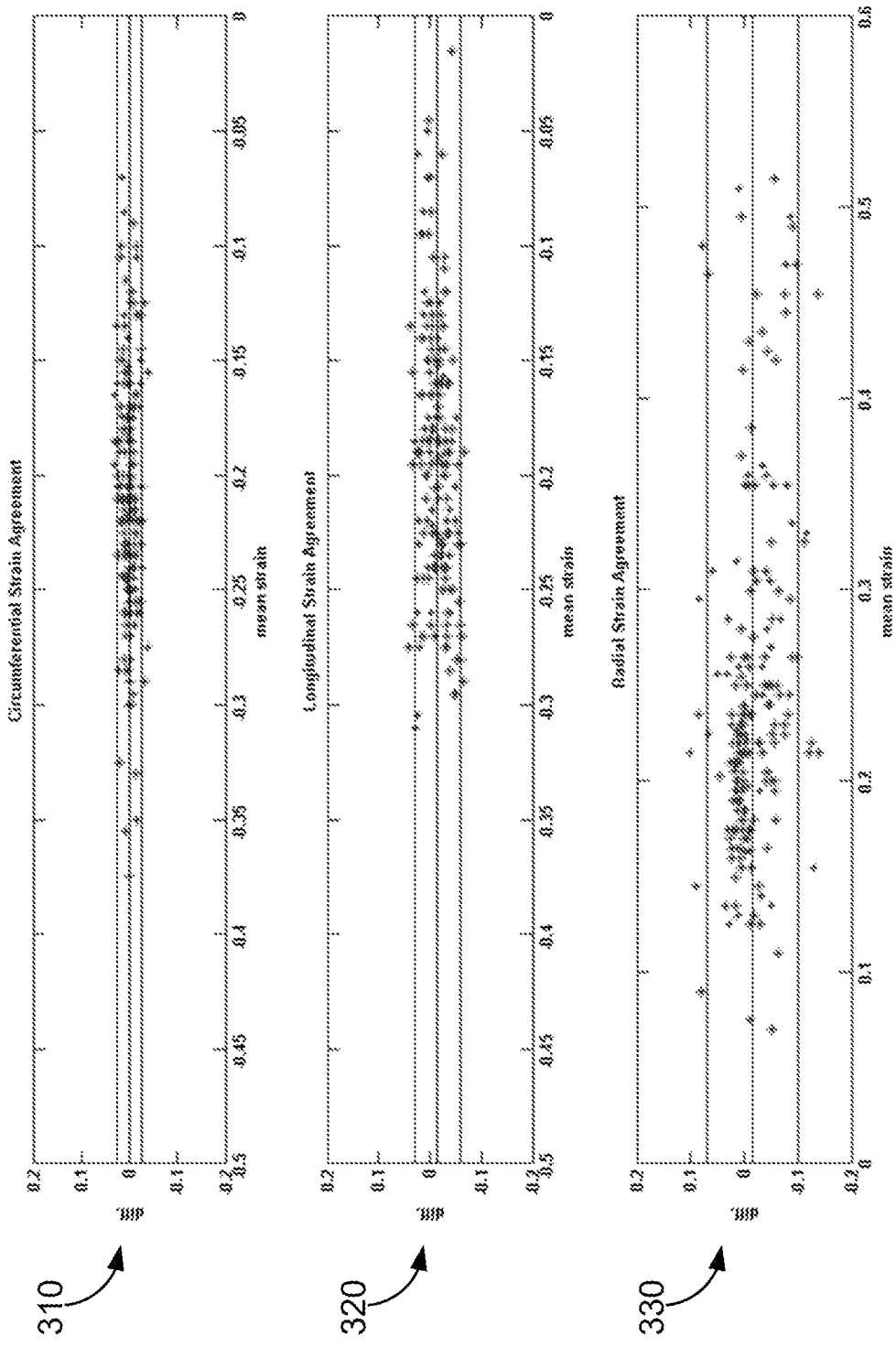
FIG. 3 is three Bland-Altman plots of the circumferential, longitudinal, and radial strain calculated in a DENSE repeatability study.
Figure 4:
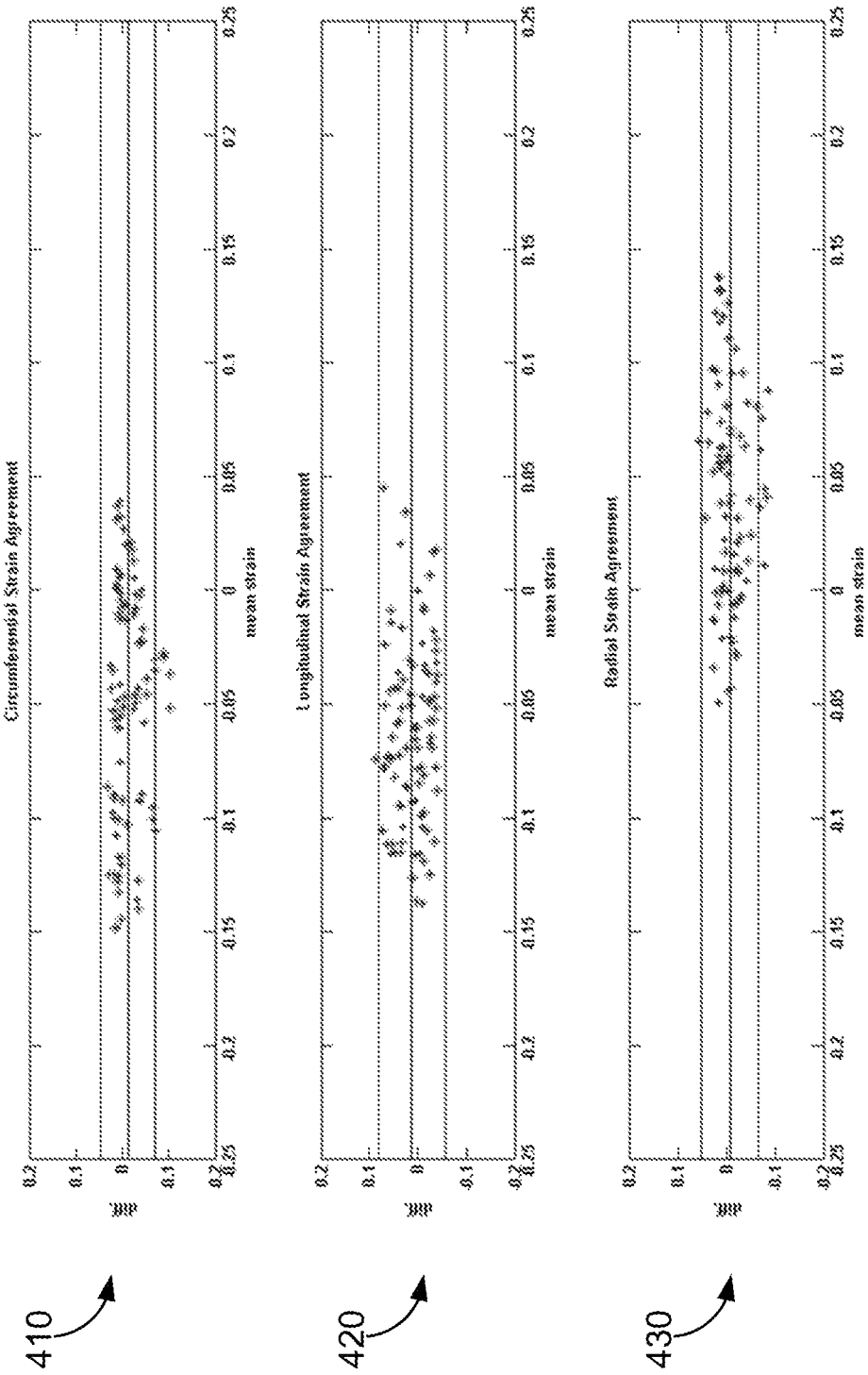
FIG. 4 is three Bland-Altman plots of the circumferential, longitudinal, and radial strain calculated in a DENSE-TMRI study of DCM patients.

Time taken for 3D myocardial segmentation in both DENSE-RPIM and TMRI was approximately 10-15 minutes per subject. Total time taken for phase unwrapping for displacements and strain analysis in DENSE-RPIM was 290±160 seconds per subject. In comparison, time taken for tissue tagging and strain analysis in TMRI averaged more than thirty minutes per subject. FIGS. 2 and 3 show Bland-Altman agreements between the DENSE-RPIM and TMRI study and the DENSE-RPIM repeatability study, respectively, in healthy subjects in regional circumferential 210, 310, longitudinal 220, 320, and radial strains 230, 330. FIG. 4 shows Bland-Altman agreements between DENSE-RPIM and TMRI in DCM patients for the above regional strains 410, 420, 430.

The differences obtained between sequences in healthy subjects in regional strain were 0.01±0.03 in circumferential, 0.02±0.07 in longitudinal and −0.01±0.10 in radial strains. The differences in regional strains in the repeatability study were 0.0±0.02 in circumferential, −0.02±0.04 in longitudinal, and −0.02±0.08 in radial strains. The differences (95% limits of agreement) in regional strains obtained between sequences in DCM patients were −0.01±0.05 in circumferential, 0.02±0.07 in longitudinal and −0.01±0.04 in radial directions.

Figure 5A:
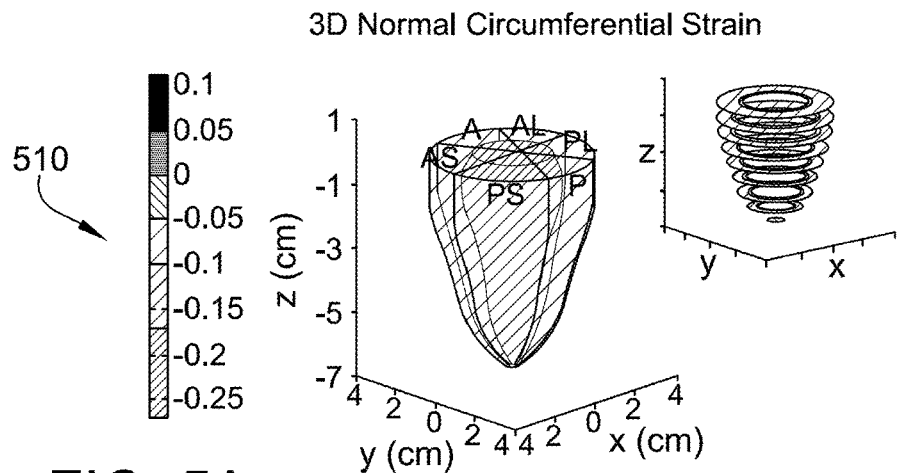
FIG. 5A shows systolic endocardial and epicardial circumferential strain estimated with DENSE-RPIM in healthy subjects.
Figure 5B:
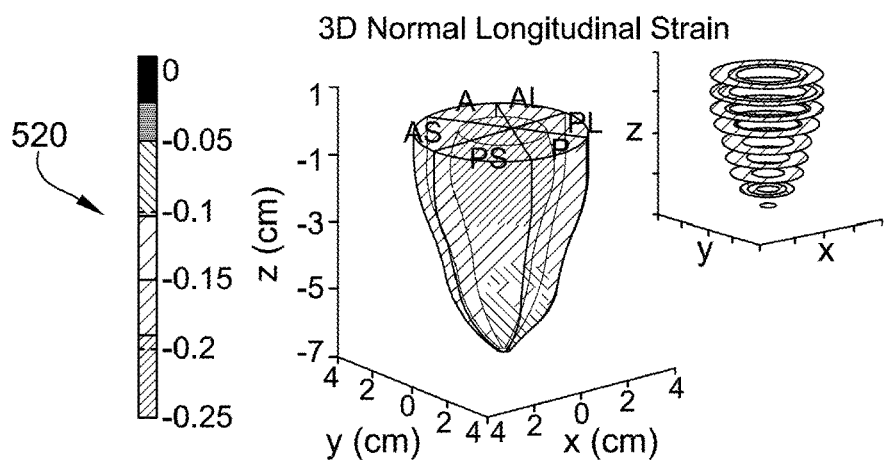
FIG. 5B shows systolic endocardial and epicardial longitudinal strain estimated with DENSE-RPIM in healthy subjects.
Figure 5C:
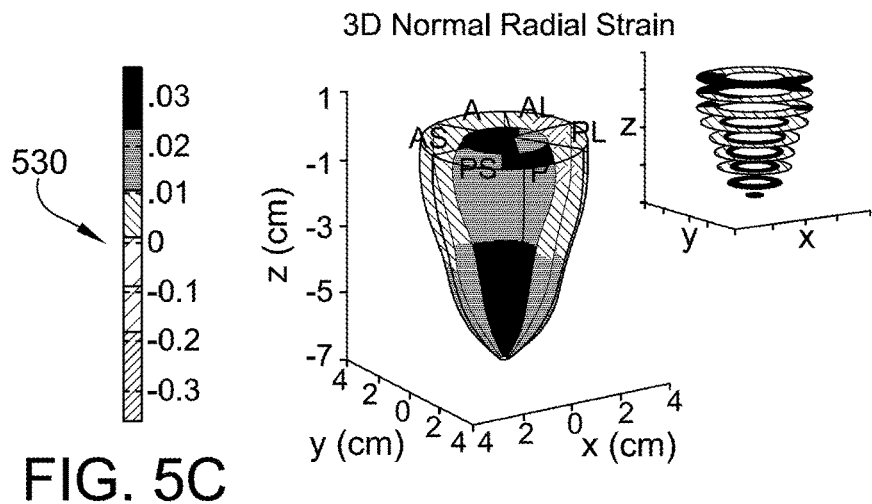
FIG. 5C shows systolic endocardial and epicardial radial strain estimated with DENSE-RPIM in healthy subjects.

FIG. 5 shows 3D contour maps of the circumferential 510, longitudinal 520, and radial strains 530 computed with RPIM and DENSE in the myocardial walls and in individual slices between the LV apex and base in a healthy subject. FIG. 6 depicts DENSE 3D strain contours in the myocardial walls in a DCM patient for circumferential strain 610, longitudinal strain 620, and radial strain 630. FIGS. 7A-R (collectively referred to as FIG. 7) shows temporal comparisons 700 of strain between DENSE-RPIM and TMRI in the sixteen AHA recommended regions in healthy subjects and FIGS. 8A-R (collectively referred to as FIG. 8) illustrates a similar comparison 800 within DCM patients spanning approximately two-thirds of the cardiac cycle. The six LV regions by column in both FIGS. 7 and 8 are, from left to right, anterior, anteroseptal, posteroseptal, posterior, posterolateral, and anterolateral.

Significant differences in means were found between DENSE-RPIM and TMRI in all three circumferential longitudinal and radial strains (P<0.01) in both healthy subjects and DCM patients. The DENSE-RPIM repeatability study showed significantly different means in longitudinal and radial strains (P<0.05) but not in circumferential strain (P=0.09). FIG. 9 is a table 900 regional strain averages and twist and torsion angles computed with DENSE-RPIM in healthy subjects and FIG. 10 is a table 1000 with similar information associated with the DCM patients. Substantial reductions in all three strain components (circumferential, longitudinal and radial) can be seen in DCM patients in the table 1000 in comparison to healthy subjects in the table 900 shown in FIG. 9. The table 1000 shows reduced apical and more clockwise basal direction of net rotations (twist) in DCM patients compared with healthy subjects in the table 900. Similar differences in torsion may be seen between DCM patients and healthy subjects.

Peak end-systolic strains were measured in sixteen regions within reconstructed 3D LV geometries in human subject experiments and Bland-Altman analysis conducted to show there is agreement between the sequences and in the repeatability study. The example study may indicate that real time computation of 3D regional strain is possible using rapid unwrapping of phases and the RPIM framework. In comparison, the RPIM post-processing technique can finish twice as fast as TMRI-Harmonic Phase (HARP) post-processing techniques that use phase unwrapping like the Strain from Unwrapped Phases (SUP) technique. The regional circumferential, longitudinal, and radial strains measured in healthy subjects were found similar to typical results found within the art.

Additionally, the order of the regional distribution of circumferential strains computed with DENSE-RPIM, with the highest values in the lateral region followed by posterior, anterior, and septal regions, is a distinguishable pattern shown in past studies within the art with healthy subjects. The circumferential strain distribution 510 in a healthy subject in the 3D contour map shown in FIG. 5 may indicate prominent endocardial to epicardial strain gradients that were observed in previous studies within the art. The mean difference in circumferential strain between DENSE-RPIM and TMRI reciprocate a range found in similar two dimensional (2D) comparison studies.

The limits of agreement (LA) found for radial strain agreements were more precise in comparison to historically observed patterns of higher variations in radial strains. Radial strain variations between the DENSE-RPIM and TMRI sequences can be propagated by naturally varying transmural kinematics of the myocardium such as large transmural strain gradients and substantially varying systolic radial wall thickening, or technical differences like the real-time demodulation of RF signals in DENSE-RPIM comparative to TMRI (or HARP) post-processing techniques. However, variations in strain computations are also influenced by the technique used for numerical analysis. Better agreement between radial strains in the example study is due to the RBFs added to the RPIM technique which introduced the advantage of avoiding singularities associated with only polynomial bases.

As described above with respect to healthy subjects, the results of the DCM patients are similar to previous studies in this area including abnormal values of both circumferential and longitudinal shortening in the septal walls when compared with the relatively healthy values in the lateral walls. It can also be seen that while symmetry was not compromised in remodeling the 3D LV geometries with DCM, regional and transmural myocardial contractile function occur heterogeneously in DCM patients.

Similar strain-time plots of DENSE-RPIM and TMRI as in FIGS. 7 and 8 demonstrate that DENSE-RPIM, which encodes displacement of discrete points as phase shifts, can be reliably used for tracking the progression of regional myocardial strains for two-thirds of the cardiac cycle in both healthy subjects and DCM patients. Reduced radial strains corresponding to reduced torsions in DCM were found in the example study which was also coincidental with better agreement between DENSE-RPIM and TMRI radial strains in DCM. Additionally, low magnitude (compared with healthy subjects) and almost identical radial strain trajectories with DENSE-RPIM and TMRI were shown in a DCM patient.

Given the above trends, it is postulated that impaired transmural mechanics (evidenced by reduced twist and torsion) in DCM reduced radial strain magnitudes and apparently contributed to better agreement in radial strains between sequences. Past studies have also investigated similar relationships between radial strains (displacements) and torsions (twists) with one study showing a linear correlation between torsion and radial displacement in both healthy subjects and elite athletes and another study in ionotropic stimulants showing increases in radial strains with augmented torsion.

Most studies define the peak end-systole direction of rotation (twist) as counterclockwise at the LV apex and clockwise at the base when viewed from the LV apex. This difference in base negative to apical positive peak rotation was observed in healthy subjects during the example study and the results are similar to regional averages from other studies in DENSE, HARP, and TMRI. The reduced torsions in DCM patients are due to reductions in twists because computation of torsion is directly proportional to the difference between a twist angle in a particular segment and its corresponding one at the base. These reductions in twist and torsion angles have also been shown in previous DCM studies.

The example study shows that the proposed DENSE-RPIM method is a high spatiotemporal resolution technique that produces reliable estimates of regional strains (circumferential, longitudinal and radial), twist angles, and torsion angles that are important to the understanding of normal cardiac biomechanics and the etiology of cardiac disease in a reduced period of time. DENSE in combination with the RPIM technique is a promising noninvasive and high resolution diagnostic tool for quantifying regional myocardial biomechanics which can be a feasible tool for early detection and management of a wide range of myocardial diseases.

Another example study was conducted for comparing dimensional (2D) in vivo regional strain computed from DENSE in reference to TMRI and a study of repeatability. One goal of this study was to investigate whether a fast-track modality like DENSE was interchangeable with lower resolution TMRI sequences and associated lengthy strain analysis procedures. The purpose was to obtain agreements between DENSE and TMRI in radial and circumferential Lagrange strain, computed from functional data acquired from the same 12 healthy subjects. Establish a method for tracking discrete points in the LV, determine their 2D displacements, investigate regional circumferential and radial strains, generate strain contour maps, and validate DENSE as an appropriate alternative to TMRI were all objectives of the example study.

In addition to in vivo agreement between DENSE-TMRI, an example validation study was performed to assert the occurrence of similar radial-circumferential shear strain ($\varepsilon_{r\theta}$) between the DENSE-TMRI using a phantom rotating device. A meshfree nearest node finite element method (NNFEM) approach, a precursor to the RPIM technique, for strain computation was used to establish whether regional strains from DENSE and TMRI in the phantom agreed favorably.

Segmentation of the myocardium and phase unwrapping were performed as described above. FIGS. 11A and 11B are examples of a flood-filled quality images 1110, 1120 used in DENSE and tag lines used in TMRI, respectively. The strain analysis using NNFEM was performed in MATLAB (Mathworks Inc., Natick, Mass.). In other embodiments NNFEM is performed using alternative programming languages within alternative software. The simulation accuracy of NNFEM was first compared to results from a conventional finite element analysis (FEA) known as measurement analysis (MEA). MEA is a numerical analysis technique based on piecewise polynomial approximations that employ elements of variable sizes. Comparison between the two simulation techniques was conducted using TMRI data from a phantom rotating device.

The NNFEM technique used in the validation study served as common framework for computing phantom rotating device and myocardial strains in both DENSE and TMRI. In conventional FEA, shape functions are constructed once for a whole element by using nodes belonging to that element and then accumulated into a global matrix. NNFEM is different from conventional numerical analysis techniques in that while its shape functions are constructed for each quadrature point 1130 using a set of nodes 1132 that are the nearest to the quadrature point as seen in FIG. 11C, these neighboring nodes are not necessarily all located in the same element. The advantages presented by using NNFEM include not requiring the assembly of a global stiffness matrix, as typically required in conventional FEA. In NNFEM, monomials and their coefficients contribute directly to generating shape functions which can also be constructed within simplex meshes. Other advantages include setting arbitrarily high orders of shape functions (depending on node availability) and it is known within the art that NNFEM has a competitive convergence rate compared to conventional FEA.

The following is a detailed outline of NNFEM for constructing shape functions for each quadrature point with n nearest nodes. The polynomial interpolation method can be seen as the approximation of a displacement function, $\tilde{f}(x)$, which is the displacement vector field within the myocardium. With n nearest nodes, the 2D function value at $x(x, y)$ can be approximated as:

$$\tilde{f}(x,y)=\Sigma_{i=1}^{n} b_i q_i(x_i,y_i) \quad (13)$$

where $q=\{q_1(x_1, y_1), \ldots, q_n(x_n, y_n)\}$ are monomial bases and $b=\{b_1, \ldots, b_n\}$ is a vector of coefficients.

The ith displacement function $f_i$, using n nodes around the central node is then expressed as:

$$q^T(x_i,y_i) \cdot b = f_i \; i=1,\ldots,n \quad (14)$$

The matrix form for $\tilde{f}=\{f_1, \ldots, f_n\}$ can then be assembled as:

$$Qb=\tilde{f} \quad (15)$$

where Q is a second order polynomial Vandermonde matrix.

Second order polynomials were chosen since linear interpolation is ill-conditioned for sparsely populated TMRI fields. The Vandermonde matrix is expressed as:

$$Q = \begin{bmatrix} 1 & x_1 & y_1 & x_1^2 & y_1^2 & x_1 y_1 \\ \ldots & \ldots & \ldots & \ldots & \ldots & \ldots \\ 1 & x_n & y_n & x_n^2 & y_n^2 & x_n y_n \end{bmatrix} \quad (16)$$

The coefficient vector b is determined by the inverse function expressed as:

$$b=Q^{-1}\tilde{f} \quad (17)$$

The approximation of Equation 13 becomes:

$$\tilde{f}(x,y)=\varnothing(x)^T \tilde{f} \quad (18)$$

where $\varnothing(x)^T=q^T Q^{-1}$ are local polynomial shape functions.

Computation of Lagrangian strain and the deformation gradient tensor, F, depends on the derivative function of $\tilde{f}(x, y)$, expressed as:

$$\frac{\partial \tilde{f}(x, y)}{\partial \alpha} = \frac{\partial q^T(x, y)}{\partial \alpha} \cdot b \; (\alpha = x, y) \quad (19)$$

To implement the above method, each pixel of interest within the myocardium is considered a quadrature point at the initial displacement time. N nearest available neighboring pixels and their position vectors are used for the shape function and to construct the matrix Q. The deformed vector $\tilde{f}$ is constructed at later phases using the corresponding deformed quadrature point and its n nearest neighbors. Q and $\tilde{f}$ are then used for computing b (in x and y coordinate directions) in Equation 17, therefore resolving all unknowns before computing derivatives. The Lagrange deformation gradient tensor, F, is computed using the four derivatives of $f(x)$ in two dimensions in Equation 19. The 2D finite strain tensor, E, is assembled from the deformation gradient tensor using the classic definition of Lagrange strain in Equation 9.

An accurate approximation of $f(x)$ is dependent on assembling the matrix of monomial bases in the Vandermonde matrix given in Equation 16. Measures taken to avoid an ill-conditioned Vandermonde matrix include (i) applying a non-singularity criterion based on rejecting a nearest node row contribution to the Vandermonde matrix if it is not linearly independent, which can be tested by locating the zero entries in the diagonal after QR factorization and (ii) using singular value decomposition (SVD) to circumvent problems with an underdetermined system. To narrow down the differences in spatial resolution between DENSE and TMRI, the TMRI tags were interpolated to obtain twice the number of original tags which reduced original tag spacing from 8.0 mm to 4.0 mm in human subjects experiments and from 4.0 mm to 2.0 mm in the phantom study.

The accuracy of the NNFEM method was tested using two different approaches. The first approach was to ensure that results of $\varepsilon_{r\theta}$ strains obtained in the phantom rotating device were similar to a three parameter analytical solution in a viscoelastic medium derived from the Navier-Stokes equation of motion in the phantom rotating device in previous studies within the art. The second approach included simulating the phantom rotating device shear strains using another more established FEA analysis technique introduced earlier as MEA.

Figures 18, 19:
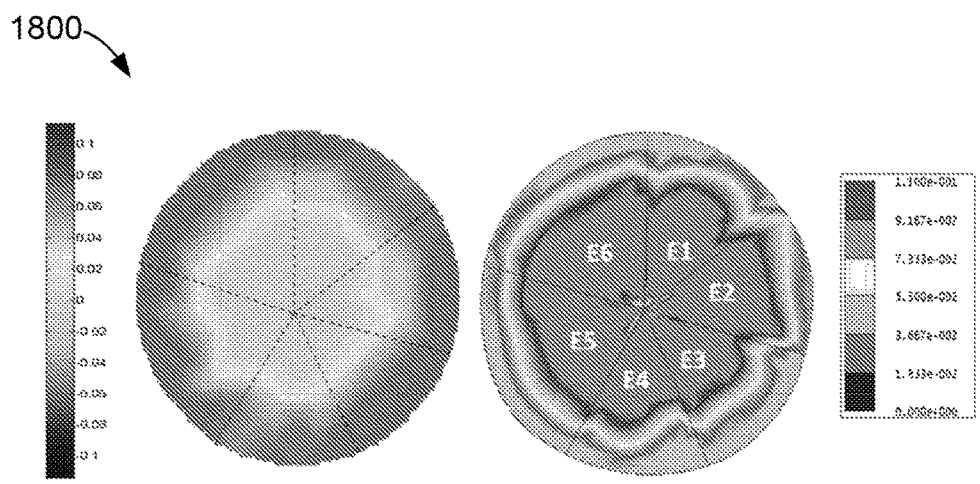
FIG. 18 shows a radial-circumferential shear strain ($\varepsilon_{r\theta}$) calculated using NNFEM (left) and MEA (right).
FIG. 19 is a table of the max and average shear strain ($\varepsilon_{r\theta}$) of NNFEM and MEA in six segments shown in FIG. 18.

MEA is an established finite element technique which was used for comparing NNFEM strain results obtained in the phantom rotating device study. MEA consists of approximating displacement components over a domain, given a set of measured displacements points, where one objective is to seek polynomial approximations for the displacement field in the least squares sense. The mapping is based on a higher order polynomial interpolation of spatial variables commonly known as the p-version in FEA which is an approximation technique known to facilitate smooth variations in displacements and strains. MEA was used to generate a 2D finite element mesh of the phantom rotating device consisting of six tetrahedral elements as shown in FIG. 18. Absolute continuity of displacements and strains were obtained across element boundaries by assembling fitted displacements from each element into a single stiffness matrix prior to solving a set of linear equations. A continuous distribution of strain was then obtained by computing the derivatives of the spatial variables and using the definition of Lagrange strain.

Displacement fields were measured in a cylinder of approximately 56 mm in radius and 202 mm in length filled with gelatin. The cylinder was then mounted in a custom rotating device and clamped in the freely rotating inner compartment of the custom rotating device. Releasing a latch to an off-axis counterweight provided torque to initiate rotation, and was followed by repeated angular acceleration of approximately 250 rad/s$^2$ provided from impact with a compliant stop. It is the angular acceleration that provided maximum $\varepsilon_{r\theta}$ strains at the outer boundary of the cylinder's gel. MR imaging was synchronized with rotation of the cylinder where a fiber optic sensor detected release of the latch and triggered the MRI pulse sequence. The MR-compatible material used for the phantom rotating device experiment was Gelatin (Knox, Camden, N.J.), which was preset in a capped acrylic cylinder at 10° C. for slightly less than a day prior to experimentation.

For the DENSE phantom rotating device study, cine data was acquired with displacement encoding applied in two orthogonal in-plane directions and 2D displacements encoded in the phase images. A DENSE sequence, known as "a_CV_epi_DENSE_611", a cine echo planar imaging (EPI) sequence employing phase cycling to suppress an artifact-generating echo, was used in the phantom rotating device study. Acquisition matrix size was 64×64 with 3.13 mm (square) pixel spacing, FOV of 200×200 mm$^2$ and 20° of flip angle. 135 phases at 6 ms of TR, 3.7 ms of TE and ETL of one were acquired in x and y encoding directions. An optimal displacement encoding frequency ($k_e$) was chosen as 0.1 cycles/mm which was a value selected based on prior studies.

Human subject cine DENSE images were acquired in multi-level short-axis imaging planes, at approximately 10-12 short-axis images per subject depending on individual LV size and using the same EPI sequence as the phantom rotating device studies. The imaging parameters used included FOV of 359×269 mm$^2$, effective TE of 8.0 ms, TR of 32.5 ms, ETL of nine, matrix size of 112×84 pixels, 3.2 mm pixel spacing, 8 mm slice thickness and 12-22 cardiac phases. Scans were acquired in breath holds of 20-30 heartbeats per encoding direction. Human subject cine DENSE and TMRI scans were also performed in the same scanner as the phantom rotating device. The same healthy human subjects and similar Bland-Altman statistical analyses were used as in the previous study.

Figure 12A:
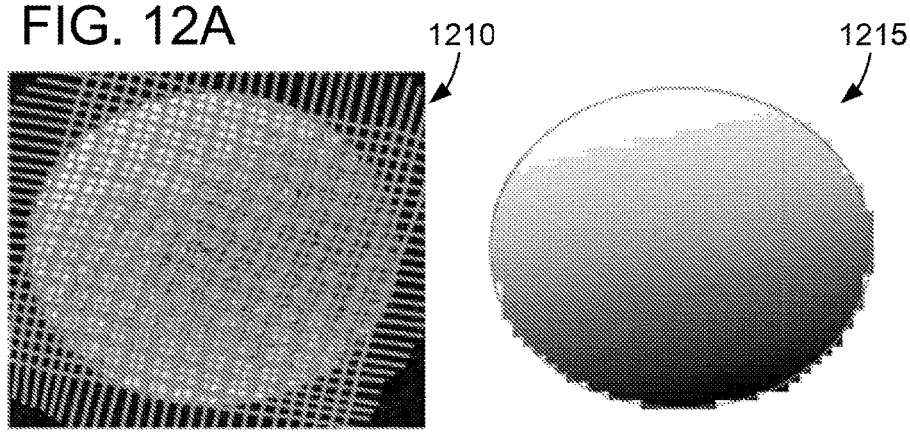
FIG. 12A is a side-by-side view of tags in TMRI (left) and phase unwrapping in DENSE (right).
Figure 12B:
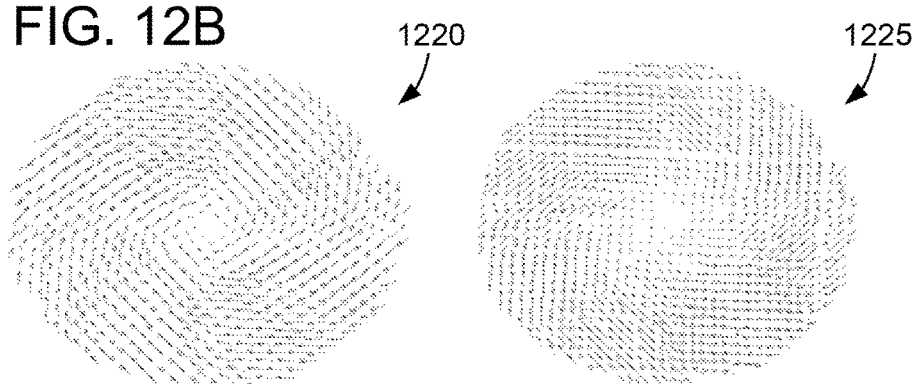
FIG. 12B is a side-by-side view of displacements at maximum shear strain ($\varepsilon_{r\theta}$) in TMRI (left) and DENSE (right).
Figure 12C:
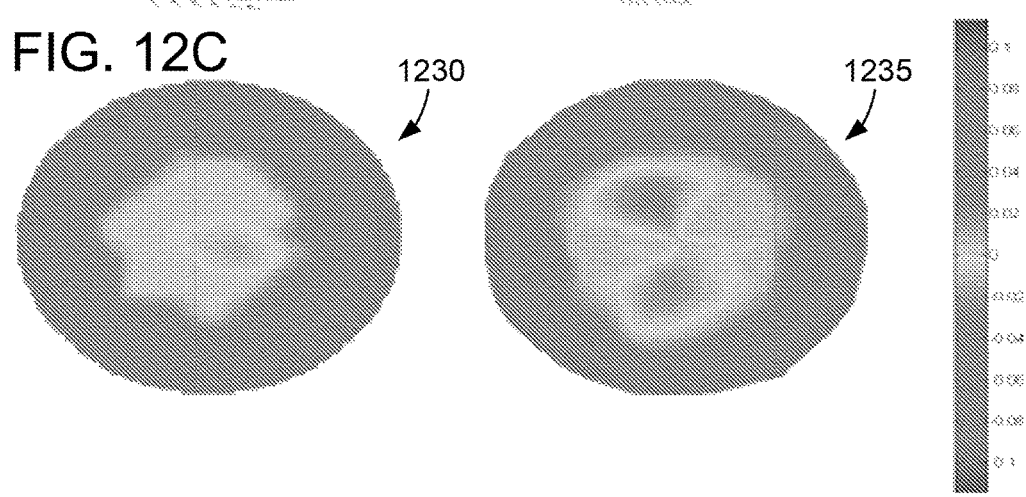
FIG. 12C is a side-by-side view of contours of maximum shear strain ($\varepsilon_{r\theta}$) in TMRI (left) and DENSE (right).

FIG. 12A shows deformed (interpolated) tags 1210 and an unwrapped phase map 1215 in the phase-encoding direction in DENSE at maximum $\varepsilon_{r\theta}$ in the phantom rotating device validation experiments. FIG. 12B illustrates TMRI displacements using original and interpolated tags 1220 and DENSE displacement maps 1225. FIG. 12C depicts contours of maximum $\varepsilon_{r\theta}$ strains in the phantom rotating device study in both TMRI 1230 and DENSE 1235.

Maximum shear strains computed with NNFEM in the phantom rotating device was ~11% for both DENSE and TMRI. Higher outer bands of shear in both DENSE and TMRI can be seen as a result of the outer torque applied to rotate the cylinder. Average HR monitored for the duration of the comparison studies was 68.0±8.1 bpm and average BP was 128.4±18.7/79.7±13.1 mmHg Average HR monitored for the duration of the repeatability studies was 68.7±7.2 bpm and average BP was 124.3±11.2/76.5±7.3 mmHg.

Figure 13A:
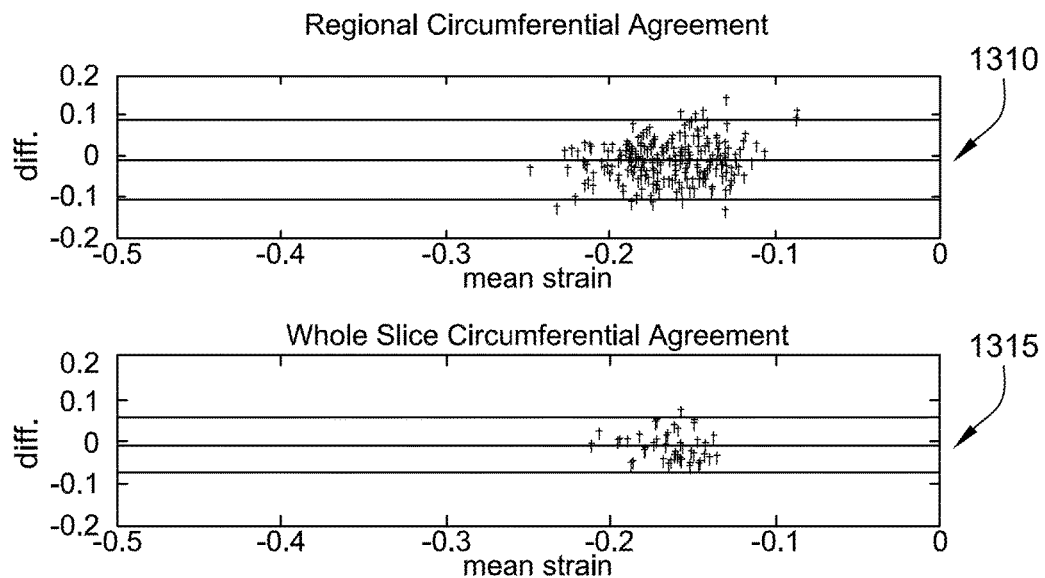
FIG. 13A shows Bland-Altman agreement from DENSE-TMRI comparison studies in human subjects for regional and whole slice circumferential strains.
Figure 13B:
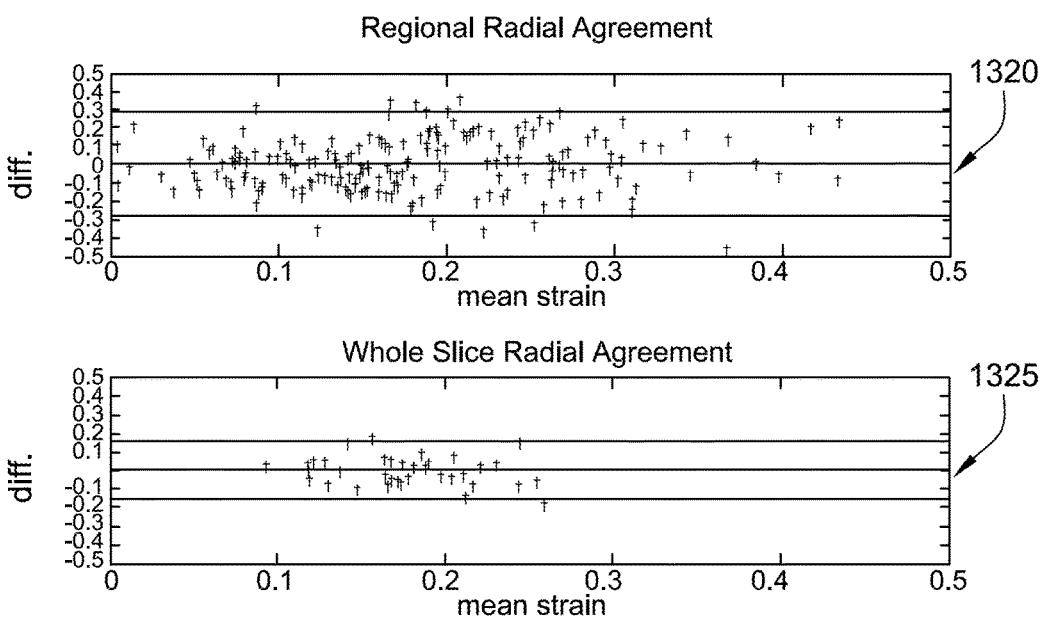
FIG. 13B shows Bland-Altman agreement from DENSE-TMRI comparison studies in human subjects for regional and whole slice radial strains.
Figure 14A:
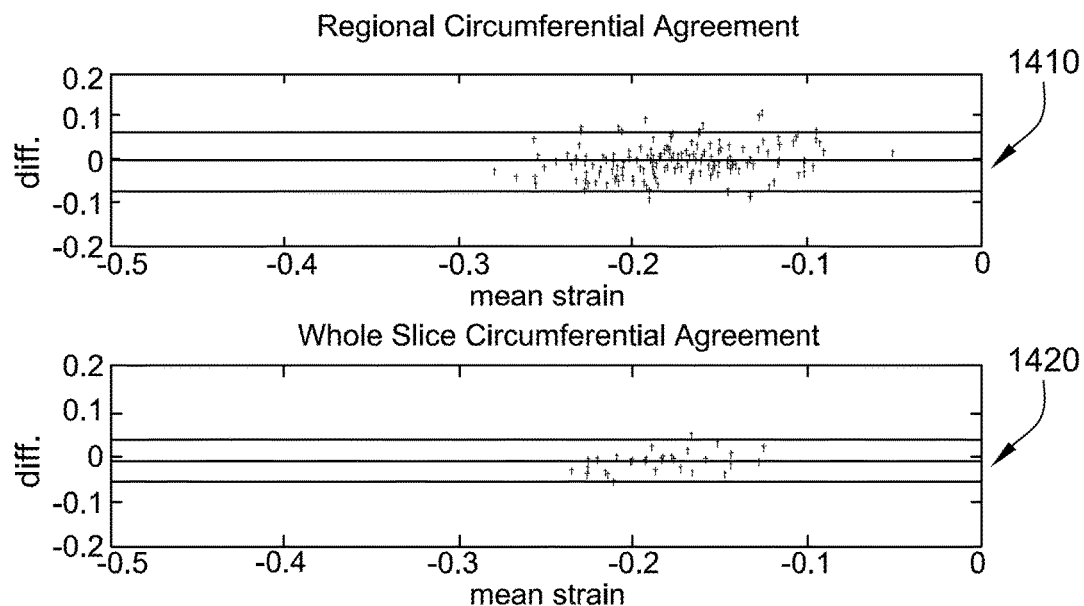
FIG. 14A shows Bland-Altman agreement from the DENSE repeatability studies in human subjects for regional and whole slice circumferential strains.
Figure 14B:
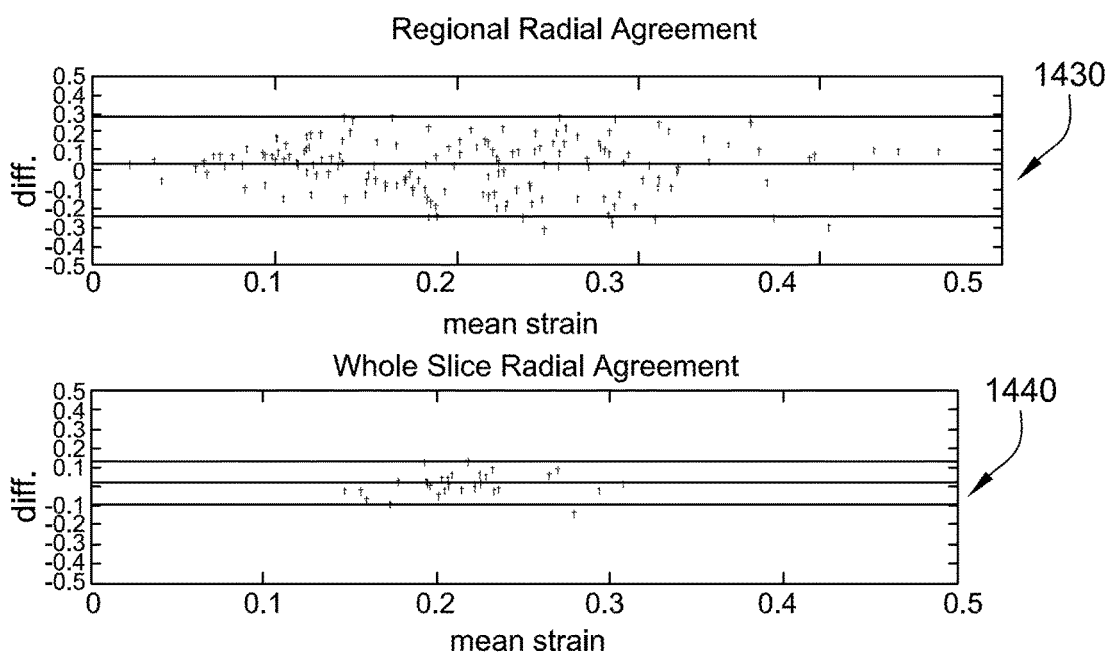
FIG. 14B shows Bland-Altman agreement from the DENSE repeatability studies in human subjects for regional and whole slice radial strains.

FIG. 13A are Bland-Altman agreements between DENSE and TMRI studies in regional 1310 and whole slice 1315 circumferential strains and FIG. 13B are Bland-Altman agreements between DENSE and TMRI studies in regional 1320 and whole slice 1325 radial strains. FIGS. 14A and 14B (collectively referred to as FIG. 14) show Bland-Altman agreements 1410, 1420, 1430, 1440 in repeatability studies in regional and whole slice circumferential and radial strains. The differences and mean values of strains from both comparison and repeatability studies were uncorrelated with P>0.05.

Figures 16A, 16B:
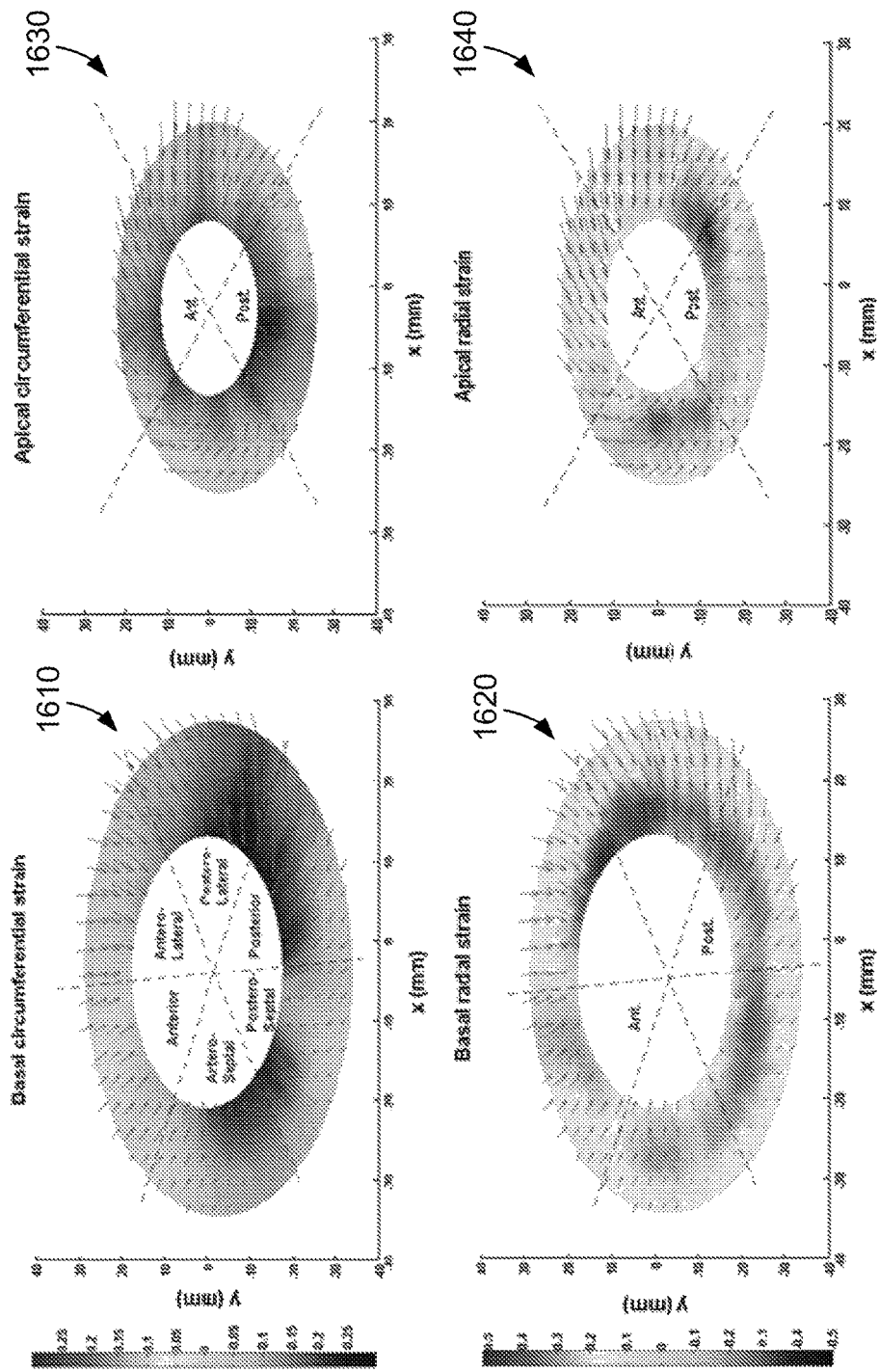

FIGS. 15A-B (collectively referred to as FIG. 15) depicts displacements and contour maps 1510, 1520, 1530, 1540 of the circumferential and radial strains computed with NNFEM from both DENSE and TMRI in the mid-ventricular slice with each slice divided into six regions. Similar to FIG. 15, FIG. 16 illustrates exemplary DENSE displacements and strain contour maps 1610, 1620, 1630, 1640 in a basal slice (divided into six regions) and an apical slice (divided into four regions). FIG. 17 is a table of regional strain averages from the DENSE-TMRI comparison and DENSE repeatability studies where it is seen that the variability (given by the standard deviation) in radial strains is higher than those in circumferential strains.

The differences obtained between DENSE-TMRI using Bland-Altman analyses in regional strain were −0.01±0.09 in circumferential and 0.01±0.29 in radial strains. The confidence ranges were further narrowed in whole slice agreements which were −0.01±0.06 in circumferential and 0.01±0.16 in radial strains. The differences in regional strains in the repeatability studies were −0.01±0.07 in circumferential and 0.02±0.27 in radial strains. The confidence ranges were narrower in whole slice agreements which were −0.01±0.05 in circumferential and 0.02±0.12 in radial strains. Paired student t-tests conducted between DENSE and TMRI showed significant differences in means in circumferential strain (P<0.005) but not in radial strain (P=0.2). Similar results were obtained from paired Student's t-tests in DENSE repeatability studies showing significantly different means in circumferential strain (P<0.005) but not in radial strain (P=0.1). FIG. 18 shows a contour map 1800 of shear strain computed with MEA on TMRI data in the phantom rotating device study. FIG. 19 is a table 1900 including the $\varepsilon_{r\theta}$ strains with NNFEM and MEA.

Computation of $\varepsilon_{r\theta}$ strains propagated by angular acceleration of the outer boundary of a gelatinous (cylinder) sample was used for validation because the solution has been described previously within the art and shear strain analysis for validating MRI techniques have been used previously within the art. Angular accelerations of the gel cylinder in this study were recorded directly from linear acceleration measurements. FIG. 12 shows an agreement between DENSE and TMRI $\varepsilon_{r\theta}$ strains computed with NNFEM in the phantom rotating device study using the gelatinous sample. Additionally, the estimated $\varepsilon_{r\theta}$ strains were found similar to simulations of an analytical solution of previous studies within the art. In general, the effectiveness of a phantom rotating device is dependent on the techniques of data measurement and numerical simulations used to match an existing analytical solution.

With in vivo DENSE-TMRI comparison and repeatability studies, peak end-systolic regional strains were measured in apical, mid-ventricular, and basal slices. The Bland-Altman plot in FIG. 13A shows there is agreement between measurements of regional circumferential strain from DENSE-TMRI. FIG. 14A shows similar agreement between circumferential strains from the repeatability studies. These differences are further narrowed when circumferential strain is averaged over whole slices. The upper and lower LA values from both regional and whole slice analysis are comparable to ranges from similar Bland-Altman analysis in previous studies. Additionally, the order of regional distribution of circumferential strains computed with DENSE as shown in FIG. 17 is a recognizable pattern within the art as described in the preceding validation study.

Results of t-tests showed that the means of circumferential strains from the comparison and repeatability studies were significantly different. However, the means of the radial strains in both studies were similar values. The similarities in the means of radial strain may be due to their higher variability which can be seen from the standard deviations in FIG. 17 and also in the Bland-Altman plots of FIGS. 13B and 14B with broader confidence ranges or LA. Explanations for the variations in radial strains exceeding expectations are given in the preceding study. Additionally, differences and mean values from the DENSE-TMRI comparison of FIG. 13 and the repeatability studies of FIG. 14 were uncorrelated (P>0.05), indicating the unlikelihood of differences in strains increasing with increasing magnitudes.

The validation study shows that NNFEM provides accurate and real time analysis of cardiac strain using polynomial shape functions and their derivatives where shape functions can be quickly constructed using nodes in a compact support domain. One significant advantage of NNFEM is in avoiding mesh generation required in conventional FEA. Interpolation at a NNFEM node is performed over an influence domain of the point while FEA meshes consisting of simplexes are easily generated but low order and slow to converge.

The validation study showed that $\varepsilon_{r\theta}$ strain computed with DENSE images in a phantom rotating device study was similar to TMRI (standard) strains. Agreements in regional myocardial strain between DENSE and TMRI, computed in sixteen AHA recommended segments were established. The validation study also established reliability in DENSE using repeatability studies. The validation study shows that DENSE in combination with NNFEM is a technique that produces high resolution estimates of both circumferential and radial strains in healthy human subjects that can be used to identify regional myocardial regional abnormalities in pathological conditions like ischemia, cardiomyopathy and other cardiac conditions like aortic insufficiency.

It is to be understood that the example study and the validation study are for exemplary purposes only and other systems and methods may be used to perform 3D cardiac strain analysis, including those described elsewhere herein.

Figure 20:
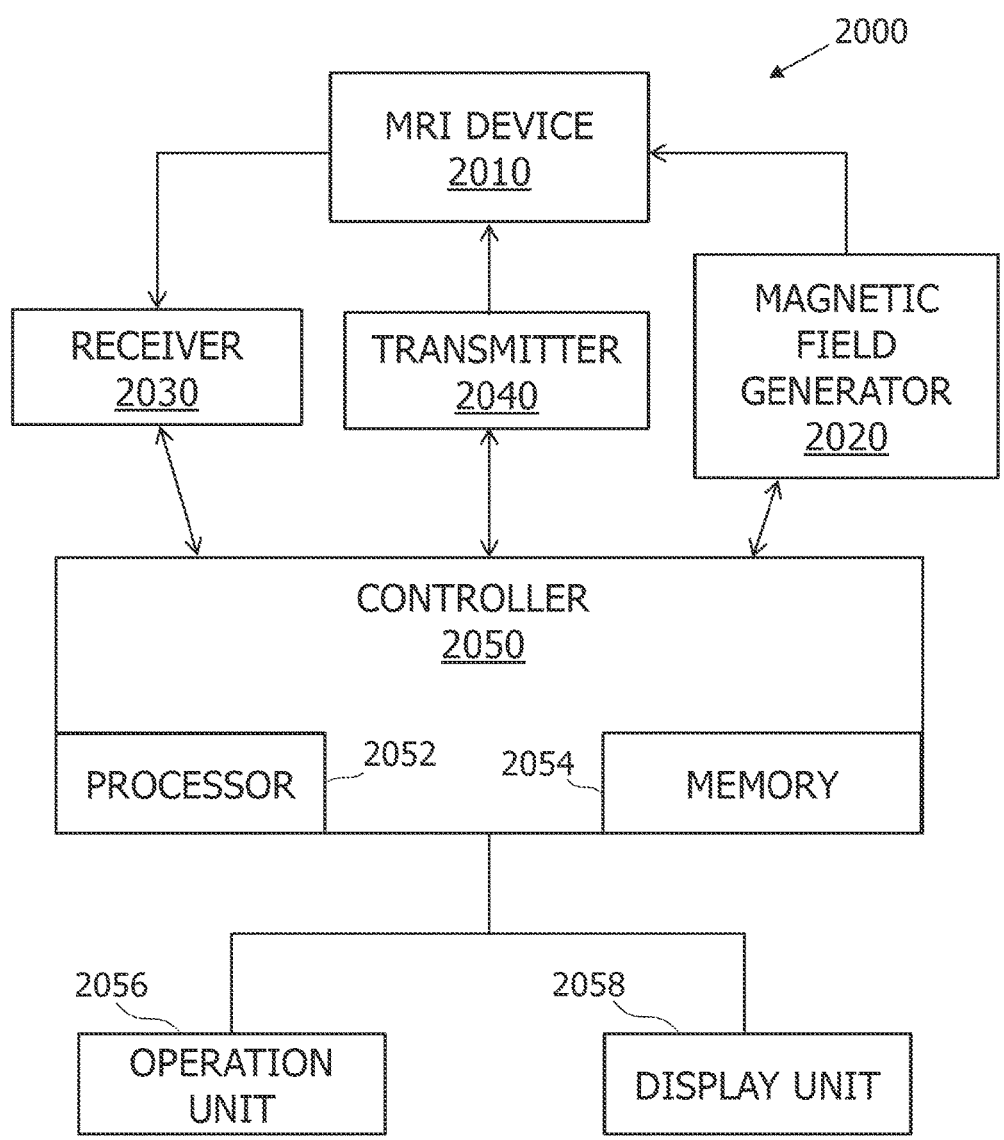
FIG. 20 is a block diagram of an MRI system.

FIG. 20 depicts an exemplary MRI system 2000. The methods, functions, and techniques described above may be implemented by an MRI system such as the system 2000. In the illustrated embodiment, the system 2000 includes an MRI device 2010, a magnetic field generator 2020, a transmitter 2030, a receiver 2040, and a controller 2050. In other embodiments, the system 2000 may include additional, fewer, or alternative components and functions to provide cardiac strain analysis, including those described elsewhere herein.

The MRI device 2010 includes at least one magnet (not shown) coupled to a plurality of coils (not shown). In the example embodiment, the MRI device 2010 includes one magnet with a bore to house a patient (not shown). In some embodiments, where the MRI device 2010 includes at least two magnets, the patient is positioned between at least one pair of magnets. The coils include a superconductive coil to produce a static magnetic field, a RF coil to produce a RF pulse, one or more gradient coils to produce a gradient magnetic field along one or more axes (e.g., x-axis, y-axis, and z-axis), and a receiving coil to capture the output signals of the MRI device 2010.

The magnetic field generator 2020 is coupled to each gradient coil of the MRI device 2010. In some embodiments, the magnetic field generator 2020 is also coupled to the superconductive coil. The magnetic field generator 2020 outputs an amplified gradient magnetic field signal to the gradient coils to induce the gradient magnetic fields. The transmitter 2030 is coupled to the RF coil to supply current to the RF coil of the MRI device 2010 to generate RF pulses.

The receiver 2040 is coupled to the receiving coil to process the output signal of the MRI device 2010. In the example embodiment, the receiver 2040 captures the output signal and converts the output signal into image data. Additionally or alternatively, the receiver 2040 may collect other types of data from the MRI device 2010, such as video data, vector data, and displacement data. The receiver 2040 is configured to transmit the data collected from the MRI device 2010 (including the captured image data) to the controller 2050 for processing and analysis.

The controller 2050 is in communication with the magnetic field generator 2020, the transmitter 2030, and the receiver 2040 to send and receive data (e.g., image data) and control information to operate the MRI device 2010. In other embodiments, the magnetic field generator 2020, the transmitter 2030, and the receiver 2040 may be integrally formed with the controller 2050. Alternatively, the controller 2050 may be in communication with the MRI device 2010 to monitor and/or control the operation of the MRI device 2050.

The controller 2050 may be any suitable controller for performing as described herein, including any suitable analog controller, digital controller, or combination of analog and digital controllers. In some embodiments, the controller 2050 includes a processor 2052 that executes instructions for software that may be loaded into a memory device. The processor 2052 may be a set of one or more processors or may include multiple processor cores, depending on the particular implementation. Further, the processor 2052 may be implemented using one or more heterogeneous processor systems in which a main processor is present with secondary processors on a single chip. In another embodiment, the processor 2052 may be a homogeneous processor system containing multiple processors of the same type. In some embodiments, the controller 2050 includes a memory device 2054.

As used herein, the memory device 2054 is any tangible piece of hardware that is capable of storing information either on a temporary basis and/or a permanent basis. The memory device 2054 may be, for example, without limitation, a random access memory and/or any other suitable volatile or non-volatile storage device. The memory device 2054 may take various forms depending on the particular implementation, and may contain one or more components or devices. In one implementation, the memory device 2054 may be or contain a computer-readable medium. For example, the memory device may be a hard drive, a flash memory, a rewritable optical disk, a rewritable magnetic tape, and/or some combination of the above. The media used by memory device also may be removable. For example, without limitation, a removable hard drive may be used for the memory device. In certain embodiments, the memory device 2054 may include remote storage such a server in communication with the controller 2050.

The memory device 2054 facilitates data storage in the MRI system 100. The memory device 2050 stores at least one computer program that, when received by the processor 2052, cause the processor 2052 to perform any of the functions of the controller 2050 described above, including processing MRI data for cardiac strain analysis. A computer program product can be tangibly embodied in an information carrier. The computer program product may also contain instructions that, when executed, perform one or more functions, such as those described herein. The information carrier is a non-transitory computer- or machine-readable medium, such as the memory device 2054 or memory on the processor 2052. Additionally, the memory 2054 is configured to facilitate storage of a plurality of images from the MRI device 2010 as processed by the controller 2050. In other embodiments, MRI device 2010 and/or magnetic field generator 2020 are controlled by a separate controller (not shown) while controller 2050 performs the methods and analysis described herein.

In the illustrated embodiment, the controller 2050 is a computing device further including an operation unit 2056 and a display unit 2058. Alternatively, the controller 2050 may not include the operation unit 2056 and/or the display unit 2058. The operation unit 124 enables a user to interface (e.g., visual, audio, touch, button presses, stylus taps, etc.) with the controller 2050 to control the operation of the MRI system 2000. In some embodiments, the operation unit 2056 is further coupled to the MRI device 2010 to control the operation of the MRI device 2010.

The display unit 2058 enables a user to view data and control information of the MRI system 2000. The display unit 2058 may further be coupled to other components of the MRI system 2000 such as the MRI device 2010. The display unit 2058 may include a visual display such as a cathode ray tube (CRT) display, liquid crystal display (LCD), light emitting diode (LED) display, or "electronic ink" display. In some embodiments, the display unit 2058 is configured to present a graphical user interface (e.g., a web browser and/or a client application) to the user. A graphical user interface may include, for example, an image display for images acquired by the MRI system 100 of a patient, operational data of the MRI system 2000, strain analysis data, and the patient's physiological data (e.g., heart rate).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for performing three-dimensional cardiac strain analysis, said method comprising:
    acquiring magnetic resonance imaging (MRI) data using a Displacement ENcoding with Stimulated Echoes (DENSE) sequence;
    segmenting the acquired MRI data;
    performing phase unwrapping on the segmented MRI data to obtain displacement data; and
    performing strain analysis on the displacement data using a meshfree numerical analysis technique.

2. A method in accordance with claim 1, wherein performing strain analysis comprises performing strain analysis using a meshfree radial point interpolation method (RPIM).

3. A method in accordance with claim 2, wherein performing strain analysis using meshfree RPIM comprises:
    applying a continuous displacement field technique to a plurality of scattered nodes of the displacement data to obtain interpolation displacement field data, the continuous displacement field technique including a radial basis function (RBF); and
    calculating a strain deformation tensor based on the interpolation displacement field data.

4. A method in accordance with claim 3, wherein calculating a strain deformation tensor based on the interpolation displacement field data further comprises:
    calculating a strain deformation tensor for at least one of circumferential strain, longitudinal strain, and radial strain based on the interpolation displacement field data.

5. A method in accordance with claim 3, wherein the RBF is a multiquadric RBF.

6. A method in accordance with claim 1, wherein acquiring MRI data comprises acquiring cine DENSE data.

7. A method in accordance with claim 1, wherein segmenting the acquired MRI data comprises segmenting the acquired MRI data into 16 regions.

8. A method in accordance with claim 1, wherein performing strain analysis comprises performing strain analysis for at least one of circumferential strain, longitudinal strain, and radial strain.

9. A method in accordance with claim 1, wherein the segmented MRI data includes an image with a plurality of local phases, and wherein performing phase unwrapping comprises:
    integrating a phase difference between each of the plurality of local phases;
    performing a discrete Fourier transform on the phase differences to obtain displacement data, the displacement data including a plurality of displacement vectors.

10. A method in accordance with claim 1 further comprising:
    identifying a first rotation angle around an axis of rotation of a first slice of the segmented MRI data;
    identifying a second rotation angle around the axis of rotation of a second slice of the segmented MRI data; and
    calculating a torsion angle based on the first rotation angle and the second rotation angle.

11. A controller coupled to a magnetic resonance imaging (MRI) device for performing three-dimensional cardiac strain analysis, the controller comprising a processor and a memory device, wherein the memory device includes instructions executable by the processor to cause the controller to:

acquire magnetic resonance imaging (MRI) data from the MRI device using a Displacement ENcoding with Stimulated Echoes (DENSE) sequence;
segment the acquired MRI data;
perform phase unwrapping on the segmented MRI data to obtain displacement data; and
perform strain analysis on the displacement data using a meshfree numerical analysis technique.

12. A controller in accordance with claim 11, wherein the memory device includes instructions executable by the processor to further cause the controller to perform strain analysis using a meshfree Radial Point Interpolation Method (RPIM).

13. A controller in accordance with claim 12, wherein the memory device includes instructions executable by the processor to further cause the controller to:
apply a continuous displacement field technique to a plurality of scattered nodes of the displacement data to obtain interpolation displacement field data, the continuous displacement field technique including a radial basis function (RBF); and
calculate a strain deformation tensor based on the interpolation displacement field data.

14. A controller in accordance with claim 13, wherein the memory device includes instructions executable by the processor to further cause the controller to:
calculate a strain deformation tensor for at least one of circumferential strain, longitudinal strain, and radial strain based on the interpolation displacement field data.

15. A controller in accordance with claim 13, wherein the RBF is a multiquadric RBF.

16. A controller in accordance with claim 11, wherein the memory device includes instructions executable by the processor to further cause the controller to acquire cine DENSE data.

17. A controller in accordance with claim 11, wherein the memory device includes instructions executable by the processor to further cause the controller to segment the acquired MRI data comprises segmenting the acquired MRI data into 16 regions.

18. A controller in accordance with claim 11, wherein the memory device includes instructions executable by the processor to further cause the controller to perform strain analysis for at least one of circumferential strain, longitudinal strain, and radial strain.

19. A controller in accordance with claim 11, wherein the memory device includes instructions executable by the processor to further cause the controller to:
integrate a phase difference between each of the plurality of local phases; and
perform a discrete Fourier transform on the phase differences to obtain displacement data, the displacement data including a plurality of displacement vectors.

20. A controller in accordance with claim 11, wherein the memory device includes instructions executable by the processor to further cause the controller to:
identify a first rotation angle around an axis of rotation of a first slice of the segmented MRI data;
identify a second rotation angle around the axis of rotation of a second slice of the segmented MRI data; and
calculate a torsion angle based on the first rotation angle and the second rotation angle.

21. A magnetic resonance imaging (MRI) system for performing three-dimensional cardiac strain analysis, said system comprising:
an MRI device configured to generate MRI data; and
a controller coupled to the MRI device, the controller including a processor and a memory device, wherein the memory device includes instructions executable by the processor to cause the controller to:
acquire the MRI data from the MRI device using a Displacement ENcoding with Stimulated Echoes (DENSE) sequence;
segment the acquired MRI data;
perform phase unwrapping on the segmented MRI data to obtain displacement data; and
perform strain analysis on the displacement data using a meshfree numerical analysis technique.

* * * * *